(12) United States Patent
Ochoa

(10) Patent No.: US 12,364,618 B2
(45) Date of Patent: Jul. 22, 2025

(54) BACK SUPPORT SYSTEM

(71) Applicant: Leonardo Ochoa, Beaverton, WA (US)

(72) Inventor: Leonardo Ochoa, Beaverton, WA (US)

(73) Assignee: Leo Ochoa, Beaverton, OR (US)

( * ) Notice: Subject to any disclaimer, the term of this patent is extended or adjusted under 35 U.S.C. 154(b) by 714 days.

(21) Appl. No.: 17/438,738

(22) PCT Filed: Mar. 13, 2020

(86) PCT No.: PCT/US2020/022744
§ 371 (c)(1),
(2) Date: Sep. 13, 2021

(87) PCT Pub. No.: WO2020/186209
PCT Pub. Date: Sep. 17, 2020

(65) Prior Publication Data
US 2022/0142803 A1 May 12, 2022

Related U.S. Application Data

(60) Provisional application No. 62/818,079, filed on Mar. 13, 2019.

(51) Int. Cl.
A61F 5/02 (2006.01)

(52) U.S. Cl.
CPC .............. A61F 5/026 (2013.01); A61F 5/024 (2013.01)

(58) Field of Classification Search
CPC .. A61F 5/02; A61F 5/022; A61F 5/024; A61F 5/026; A61F 5/028; A61F 5/30; A61F 5/32; A45F 3/00–06; A45F 3/08; A45F 3/10; A45F 2003/127; A41D 13/0531; A41D 13/0512; A61H 1/0292
USPC .......................................................... 602/19
See application file for complete search history.

(56) References Cited

U.S. PATENT DOCUMENTS

| | | | |
|---|---|---|---|
| 26,628 A * | 12/1859 | Taylor | A61F 5/028 602/19 |
| 8,926,537 B2 * | 1/2015 | Ingimundarson | A61F 5/028 602/19 |
| 2004/0059267 A1 | 3/2004 | Kancilja et al. | |
| 2010/0204630 A1 | 8/2010 | Sandifer et al. | |
| 2011/0290843 A1* | 12/2011 | Sagan | A45F 3/04 224/645 |

(Continued)

FOREIGN PATENT DOCUMENTS

WO WO-2020186209 A1 9/2020

OTHER PUBLICATIONS

"International Application Serial No. PCT/US2020/022744, International Search Report mailed Jun. 3, 2020", 2 pgs.

(Continued)

Primary Examiner — Alireza Nia
Assistant Examiner — Robin Han
(74) Attorney, Agent, or Firm — SCHWEGMAN LUNDBERG & WOESSNER, P.A.

(57) ABSTRACT

A back support system includes a flexible support formed in the shape of a portion of a spine of a person, the flexible support extending in an "S" shape corresponding to the shape of the spine, a brace portion coupled to the flexible support proximate ends of the flexible support, the brace portion adapted to force the spring portion toward the spine as a wearer bends, and at least one rib extending between the flexible support and the brace portion.

14 Claims, 25 Drawing Sheets

(56) References Cited

U.S. PATENT DOCUMENTS

| | | | |
|---|---|---|---|
| 2013/0281901 A1* | 10/2013 | Ochoa | A61F 5/028 602/19 |
| 2015/0133843 A1 | 5/2015 | Turrini et al. | |
| 2016/0045387 A1* | 2/2016 | Lee | A61H 3/008 602/12 |
| 2018/0014961 A1* | 1/2018 | Mylonas | F41H 1/02 |
| 2021/0038418 A1* | 2/2021 | Mylonas | A61F 5/026 |

OTHER PUBLICATIONS

"International Application Serial No. PCT/US2020/022744, Written Opinion mailed Jun. 3, 2020", 4 pgs.

* cited by examiner

BACK SUPPORT SYSTEM

CLAIM OF PRIORITY

This patent application is a U.S. National Stage Filing under 35 U.S.C. 371 from International Application No. PCT/US2020/022744, filed on Mar. 13, 2020, and published as WO 2020/186209 on Sep. 17, 2020, which claims the benefit of priority to U.S. Provisional Application Ser. No. 62/818,079, filed Mar. 13, 2019, all of which are incorporated by reference herein in its entirety.

BACKGROUND

Emergency medical technicians (EMTs) face a related common challenge in their daily duties. The heavy lifting of medical equipment and patients up and down flights of stairs places all EMTs at risk for experiencing frequent back injuries. Current back braces are designed to lock the back muscles and spine in one position, limiting mobility, creating discomfort, and restraining the user from doing their work.

SUMMARY

A back support system includes a flexible support formed in the shape of a portion of a spine of a person, the flexible support extending in an "S" shape corresponding to the shape of the spine, a brace portion coupled to the flexible support proximate ends of the flexible support, the brace portion adapted to force the spring portion toward the spine as a wearer bends, and at least one rib extending between the flexible support and the brace portion.

A method includes placing a flexible support adjacent a spine of a wearer, the flexible support extending in an "S" shape corresponding to the shape of the spine, coupling a brace portion to the flexible support proximate ends of the flexible support, the brace portion adapted to force the spring portion toward the spine as a wearer bends, and inhibiting lateral movement of the flexible support and brace portion by providing at least one rib extending between the flexible support and the brace portion. This method adds needed support to the bottom end of the flexible support to utilize the waistline as a fulcrum point.

BRIEF DESCRIPTION OF THE DRAWINGS

FIGS. 22A and 22B show lateral movement from side to side to support the wearer's torso movement as the torso twists according to an example embodiment.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the invention, and it is to be understood that other embodiments may be utilized and that structural, logical and electrical changes may be made without departing from the scope of the present invention. The following description of example embodiments is, therefore, not to be taken in a limited sense, and the scope of the present invention is defined by the appended claims.

Figures 1, 2:
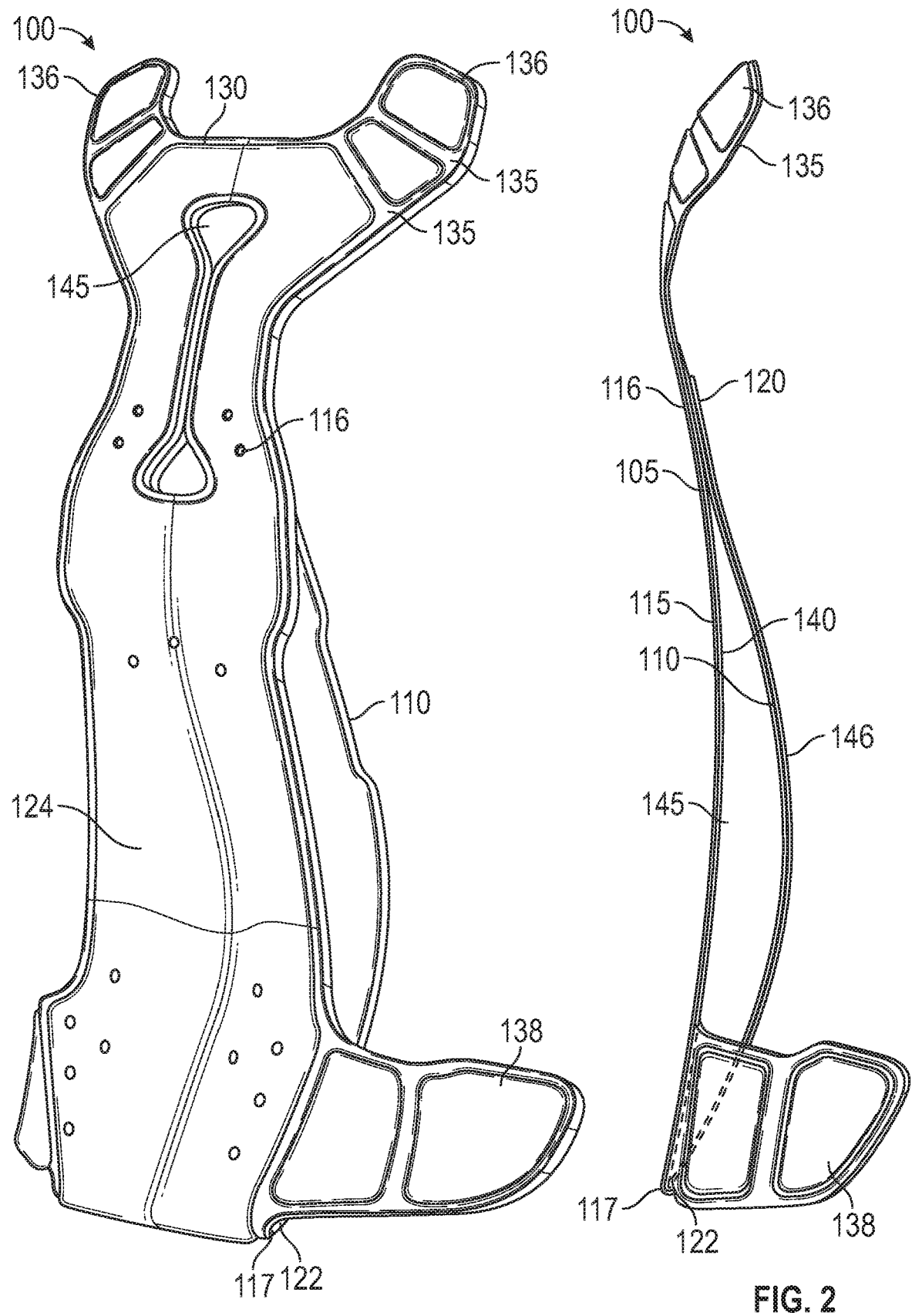
FIG. 1 is a perspective front view of a back support system having an "S" shaped flexible support with stabilizing structures according to an example embodiment.
FIG. 2 is a perspective back view of a back support system having an "S" shaped flexible support with stabilizing structures according to an example embodiment.

FIG. 1 is a perspective block diagram front view of a back support system 100, also referred to as an artificial spine system. The back support system 100 has an artificial spine 105 that includes and supports a flexible front arc 110 that while in use, is placed adjacent a spine of a user to provide back support and a brace portion 115 that supports ends of the flexible front arc 110 at two support points 116 and 117. The flexible front arc 110 is thus held in a compressed position to form an arc to somewhat match the natural curvature of a spine of a wearer.

FIG. 2 is a side view of the back support system 100. In one embodiment, the flexible front arc 110, which may be thought of as a spring, is formed of a flexible, lower durometer material that has a contoured shape to conform to the normal shape of a human spine. In further embodiments, the shape may be similar to that of a human spine while providing support at one or more points along the spine. Still other shapes with multiple layers that provide support at desired points of a spine may be used in further embodiments. In one embodiment, the flexible front arc 110 has a rectangular shape and a thickness selected to provide a desired spring force, ranging in average torso sizes of 12"-19" to accommodate child to adult average sizes. In further embodiments, the flexible front arc 110 may be adjusted in length and curvature to accommodate any torso size and shape. The length of the flexible front arc 110 may be selected for each wearer to run from the base of the spine to a point short of the neck. In one embodiment, the flexible front arc 110 extends up to between the shoulder blades of the wearer.

A stiffer, higher durometer material brace portion 115 of the artificial spine 105 is coupled to the flexible support 110 at ends 120 and 122 of a length of the flexible front arc 110 and operates to push the flexible front arc 110 into the back of the wearer. The higher durometer material brace portion 115 resists bending motions of the spine, pushing the flexible front arc 110 harder into the back and spine of a wearer when the wearer is bending. It thus provides additional support of the spine when a wearer leans over to move or pick up a heavy object. The brace portion 115 may be completely rigid, bending very little if any, or may be less rigid in further embodiments, with a polyethylene low durometer of 54D or a high of 70D. The durometer may vary outside these example limits in further embodiments.

In one embodiment, the brace portion 115 includes a vertical indent indicated generally at 124 to increase the rigidity of the brace portion 115 such that it is better suited for maintaining the flexible front arc 110 in a desired flexed position. Support point 116 of the brace portion may include one or more hardware fasteners, such as rivets, or other means of retentively coupling the end 120 of the arc 110 to the brace portion 115. Support point 117 may include a curved portion into which the end 122 may be inserted. The curved portion is designed to engage with the end 122 and hold the end 122 in place to maintain the shape and spring force provided by the arc 110. Note that for transport or storage, the arc 110 may be further flexed and end 122 removed from the support point 116.

In one embodiment, the brace portion may be configured to extend from support point 117 at a lower end of the brace portion to an upper end indicated at 130. References to positions, such as lower and upper refer to an orientation of the back support system 100 as being worn by an upright standing person for convenience of description. The upper end 130 may include multiple folding hinges 135 creating a shoulder wrap portion 136 to permit that upper end 130 to wrap over a user's shoulders. The folding hinges 135 may be formed from a second layer 140 that at least partially coincides with and is coupled to the stiffer material of the brace portion 115. The hinges 135 may consist of the second layer 140 that is significantly more flexible than the stiffer brace portion 115. The lower end of the brace portion 115 may include similar folding hinges to wrap around a user's hips as indicated at waist wrap portions 138.

The brace portion 115 may also include an opening 145 positioned to provide less contact of an upper part of the brace portion 115 with the neck portion of the spine of the user and may also provide for not impeding flexing of the user in the upper back and shoulder areas.

The arc 110 when installed in the brace portion between attachment points 116 and 117 results in an open working space 146. The arc 110 may also include a softer material 146 at least partially coextensive with the arc 110 in a position that contacts the wear's back. The softer material 146 may be fabric based to cushion the spine of the user and may also have wicking properties for fluids generated by the wearer.

Figure 3:
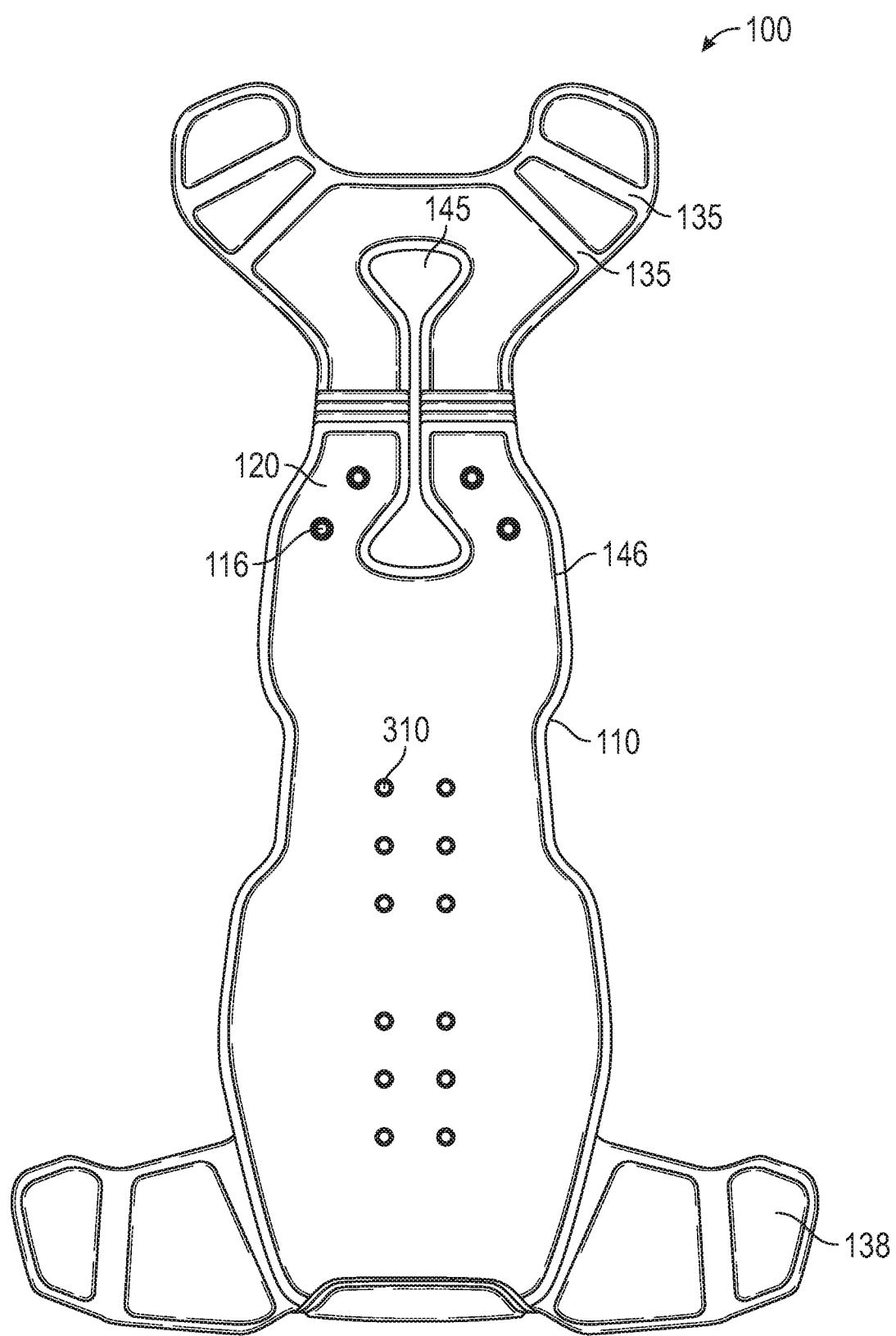
FIG. 3 is a back elevational view of a back support system according to an example embodiment.

FIG. 3 is a front elevation view of the system 100. The front of the system 100 is the part that contacts a back of the user. One or more holes 310 may be provided for breathability. A better view of the opening 145 is also visible. The opening 145 may extend between the attachment point 116 and corresponding end 120 toward the upper end of the system 100 to allow user flexibility. The shape of the opening appears to be shaped like an elongated hourglass; open polygon spaces coupled by a narrower opening. Note than just about any shape 145 will work so long as the shape 145 provides a wearer flexibility while also providing sufficient structural support for securely positioning the system 100 against the wearer.

Figure 4:
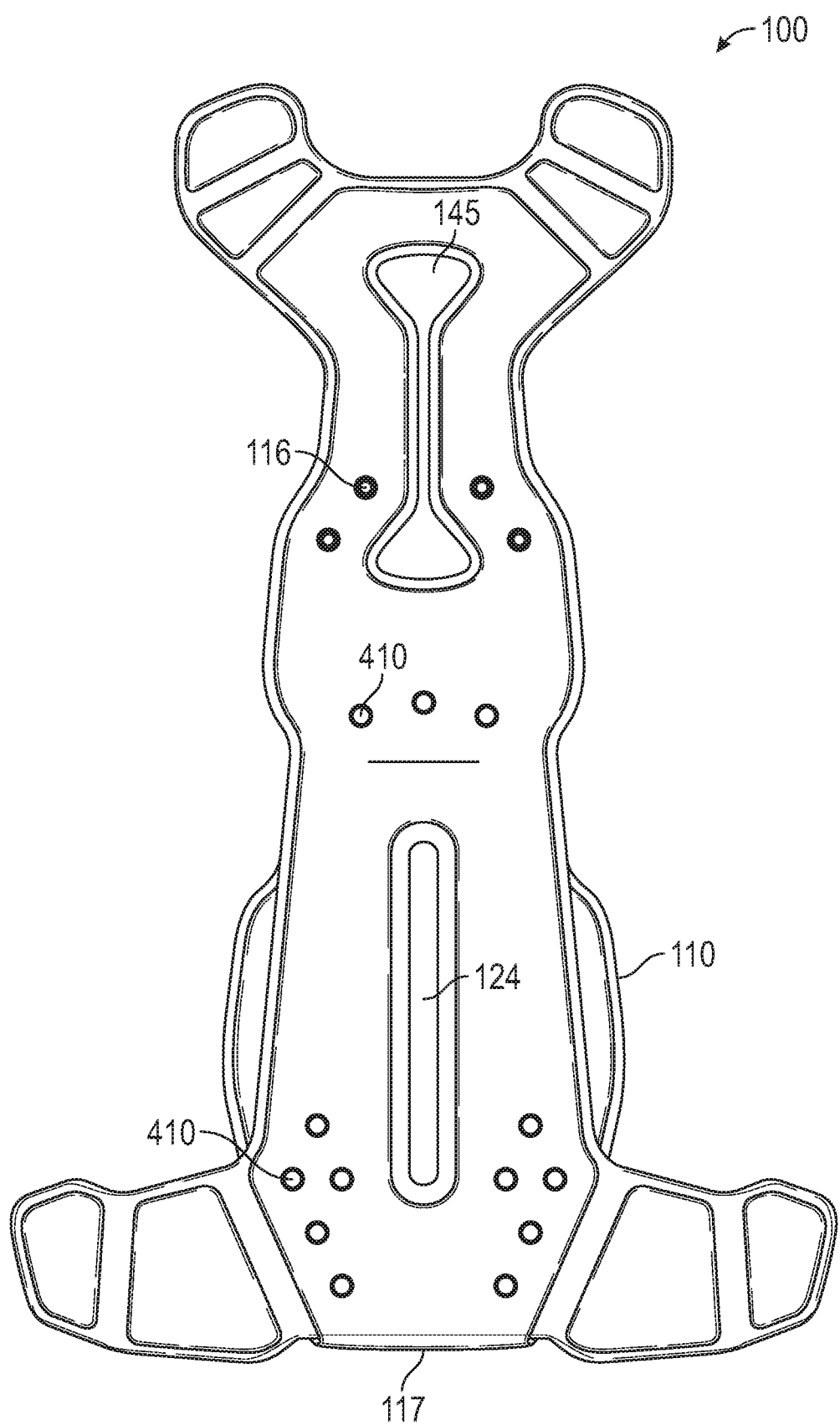
FIG. 4 is a front elevational view of a back support system according to an example embodiment.

FIG. 4 is a back elevation view of the system 100. The back of the system 100 is the part that supports the arc and is opposite the front that contacts the wearer. The vertical indent 124 is better illustrated. The vertical indent may have a curved shape, a pill or "V" shape, or other shape that is commonly used to increase structural integrity of generally planar surfaces. As shown, the vertical indent 124 extends over at least a portion of the brace portion 115 between the attachment points 116 and 117 and prevents flexing of the brace portion toward the arc 110. Several holes 410 may be used for breathability. The number and position of the holes may be varied but should be positioned to provide comfort to the user and yet not adversely affect the structural integrity of the brace portion 115.

Figures 5, 6:
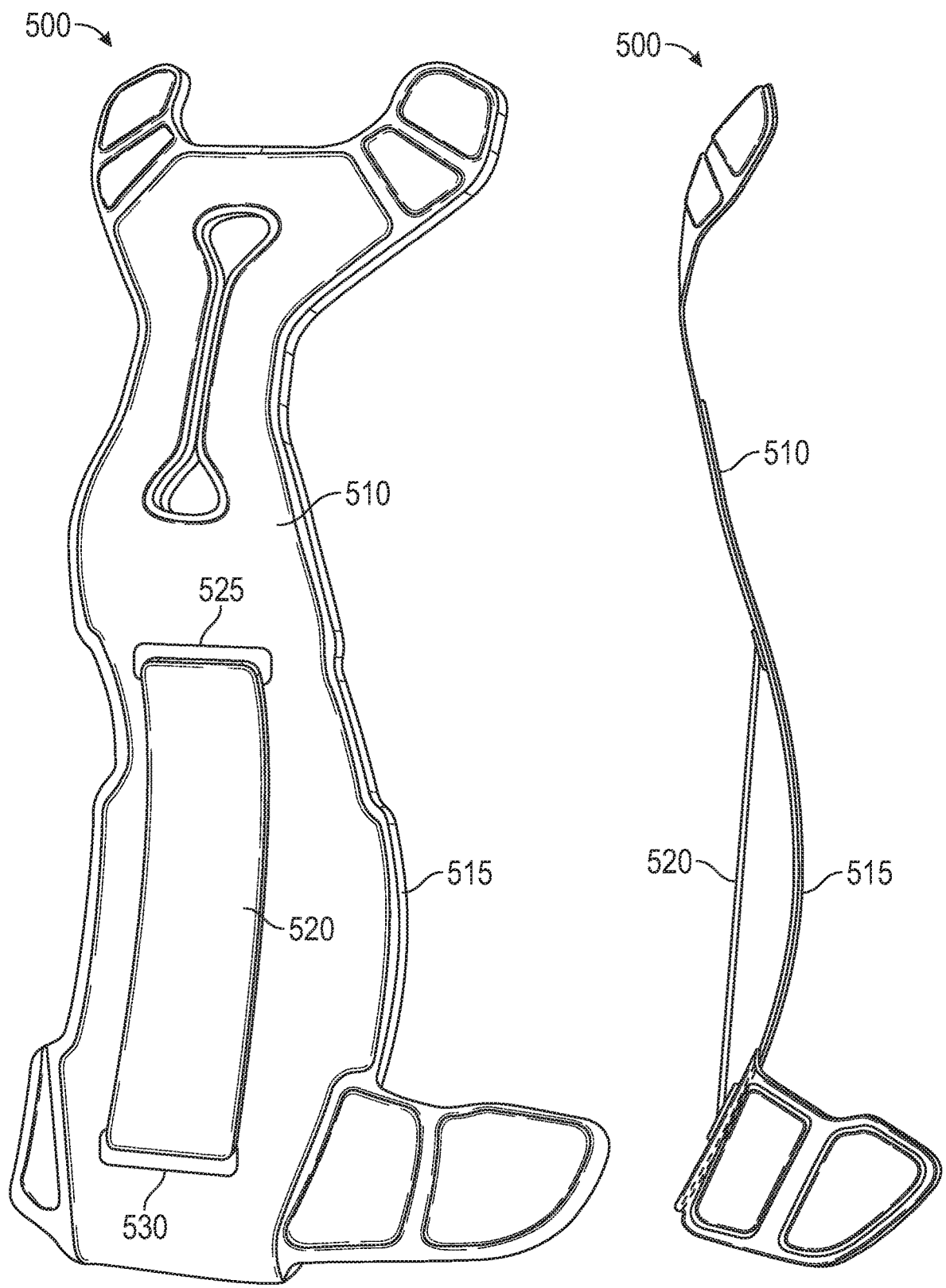
FIG. 5 is a perspective view of a back support system according to an example embodiment.
FIG. 6 is a side view of the system of FIG. 5 according to an example embodiment.

FIG. 5 is a perspective view of a back support system 500. System 500 is formed of one continuous piece 510 that includes an arc portion 515 configured to conform to a wearer's spine. System 500 includes many similar features to the brace portion 115 shown in FIGS. 1-4, except that the middle portion now is arced as shown at arc portion 515, having a similar shape as an installed arc portion 110. In addition, a band 520 is provided, opposite the arc portion 515 to tension the piece 510 to support or create the arc portion 515. The band may be attached via hardware and/or slotted openings 525 and 530 located positions similar to attachment points 116 and 117 in system 100. In some embodiments, the band may be elastic and can be formed from multiple different materials and material thicknesses to provide sufficient tension to provide the arc portion 515 with a desired spring constant. FIG. 6 is a side view of system 500.

The artificial spine 105 is designed to be worn throughout the duration of moments of heavy lifting. It is also suggested to be worn during moments of back muscle and spine fatigue. The artificial spine 105 may be built-in or attached to garments and other soft goods which may be piece of fabric shaped to fit about a lower back portion of a wearer. When built into a garment, the artificial spine and garment may be referred to as an artificial spine system or back support system.

In one embodiment, as the user bends over to lift, the artificial spine automatically adjusts to the shape of the lumbar, with brace portion 115 pushing the soft flexible arc 110 into the back and spine of the wearer, assisting the wearer in tightening their lower back muscles. While also guiding the spine and reminding the user to maintain natural spinal alignment.

Figure 7:
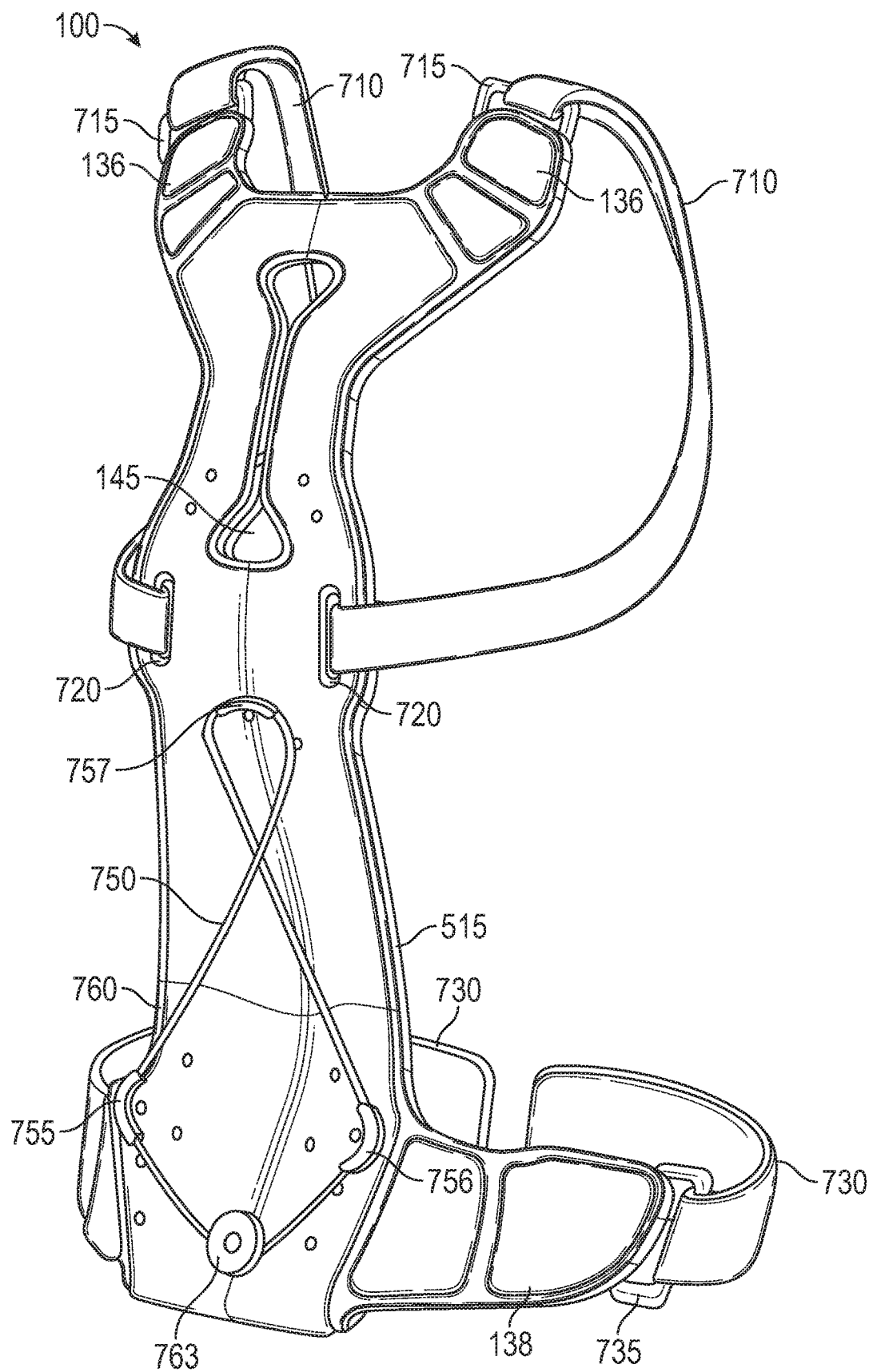
FIG. 7 is a perspective view of system with attachment straps for securing system to a wearer according to an example embodiment.

FIG. 7 is a perspective view of system 500 with attachment straps for securing system 100 to a wearer. Shoulder straps 710 may attach to the shoulder portions via a clip 715. Clip 715 may alternatively be a loop or D-ring to perform the same attachment function. The straps 710 have a length sufficient to extend over the wearer's shoulders and extend downward to couple to cutouts 720 in brace portion 115 positioned about the attachment point 116 or just below. As shown, the cutouts 720 are positioned near the outside of the brace portion just below a lower opening of the opening 145 that provides for upper back and neck flexibility.

Similarly, waist straps 730 are coupled to clips 735 to waist wrap portions 138. The two waist straps may be coupled around the waist of the wearer in an adjustable tightness manner such as by a belt buckle or fastener.

A lacing system 750 is used to adjust tension of the arc portion 515 in one embodiment. The lacing system 750 includes a pair of lower attachment points 755 and 756 set near outside edges of a lower portion 760 of the piece 515. A single upper attachment point 757 is positioned proximate the slots 720. A cable 760 is shown running from a dial 763 to the lower attachment points 755 and 756 up to the point 757. In one embodiment, the attachment points are simple curved troughs adapted to loosely fit the cable 760 such that the cable can slide through the curved troughs when tension is changed via dial 763. The cable 760 may be crossed over itself between the lower attachment points and the single upper attachment point if desired. More or fewer attachment points may be used in further embodiments provided such attachment points allow for desired tensioning via use of the dial 763. The dial may be of conventional design such that turning the dial in different direction decreases or increases tension of the cable 763.

With this built in artificial spine, the wearer can maintain natural spinal alignment to safely lift and transport the weight of heavy loads. The back support system 100 provides methods for controlling the rigidness and flexibility of the flexible arc 110 that can assist the user in all-day use. The ability of the back support system 100 to be both flexible and rigid facilitates adjustment to the normal body movements of the human spine in moments of walking, siting, twisting, bending, and lifting.

Figure 8:
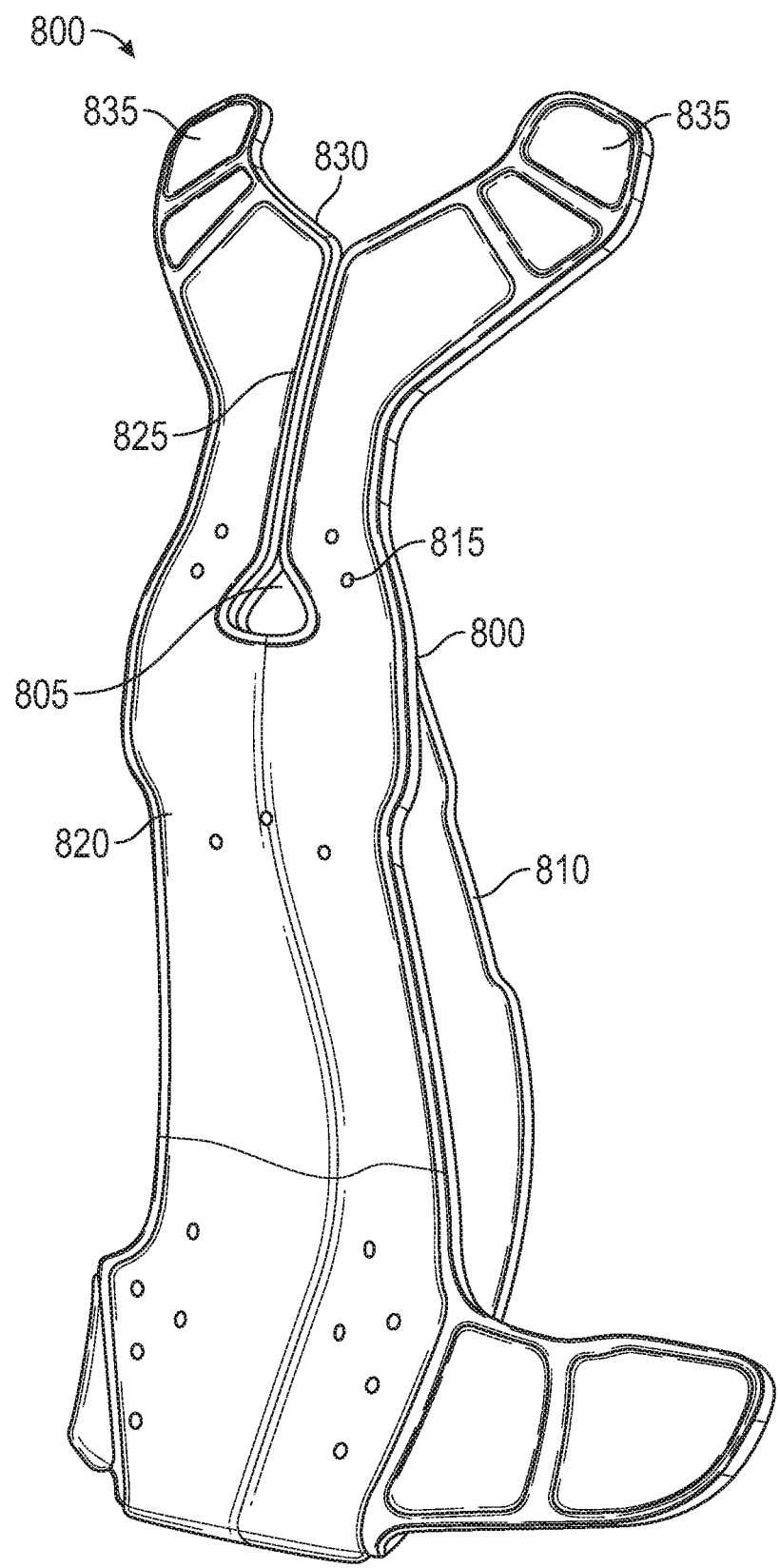
FIG. 8 is a perspective view of a system that includes a split top for added shoulder flexibility according to an example embodiment.

FIG. 8 is a perspective view of a system 800 that is similar to system 100 but includes a split top for added shoulder flexibility. An opening 805 is positioned near arc 810 upper attachment point 815 of a brace portion 820. The opening 805 includes a channel 825 extending to the top of an upper end 830 between shoulder wrap portions 835 of the brace portion 820. The channel 825 allows for independent shoulder movement of a wearer.

Figure 9:
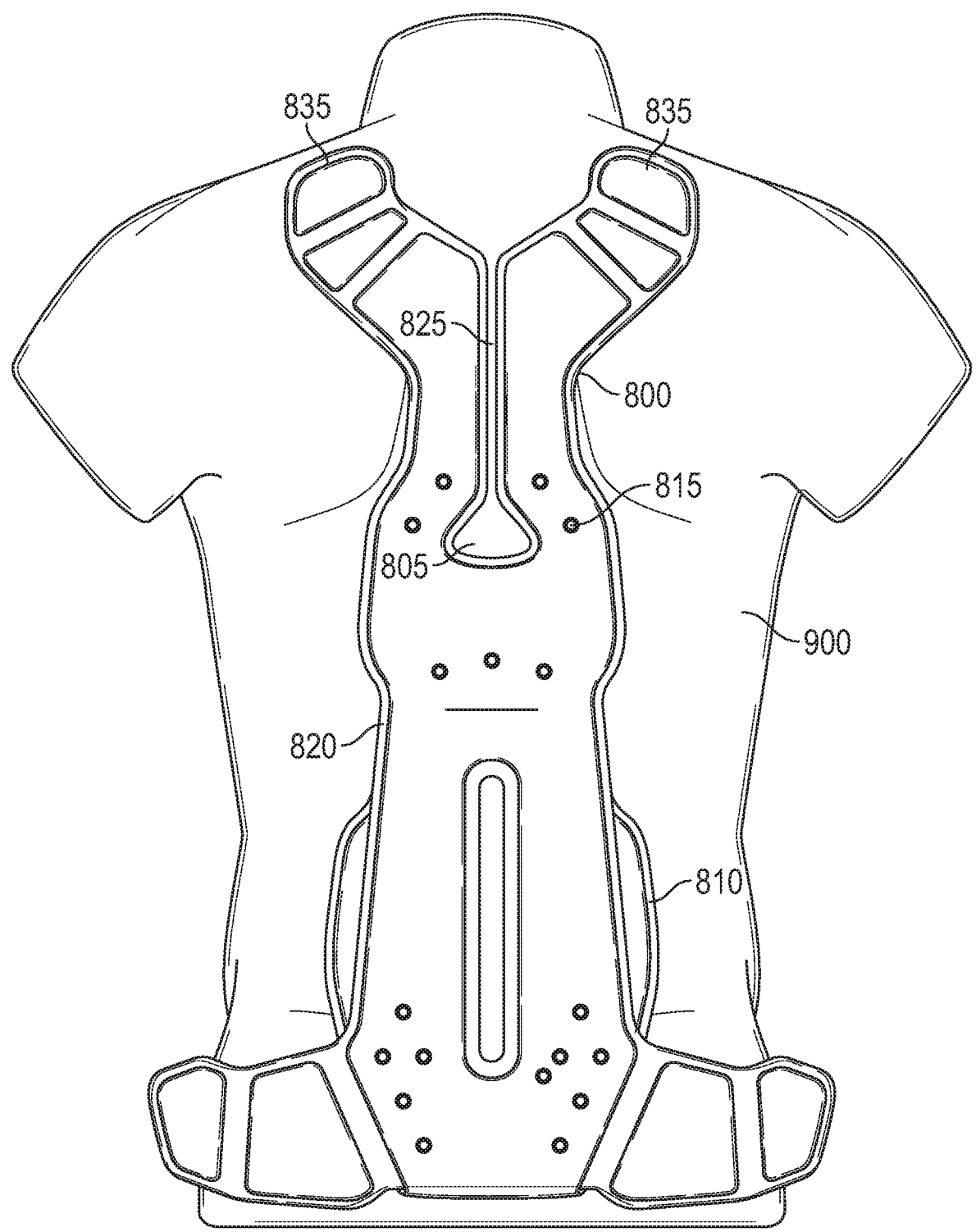
FIG. 9 is a back elevation view of the system of FIG. 8 being worn on a user according to an example embodiment.

FIG. 9 is a back elevation view of the system 800 being worn on a user 900.

Figure 10:
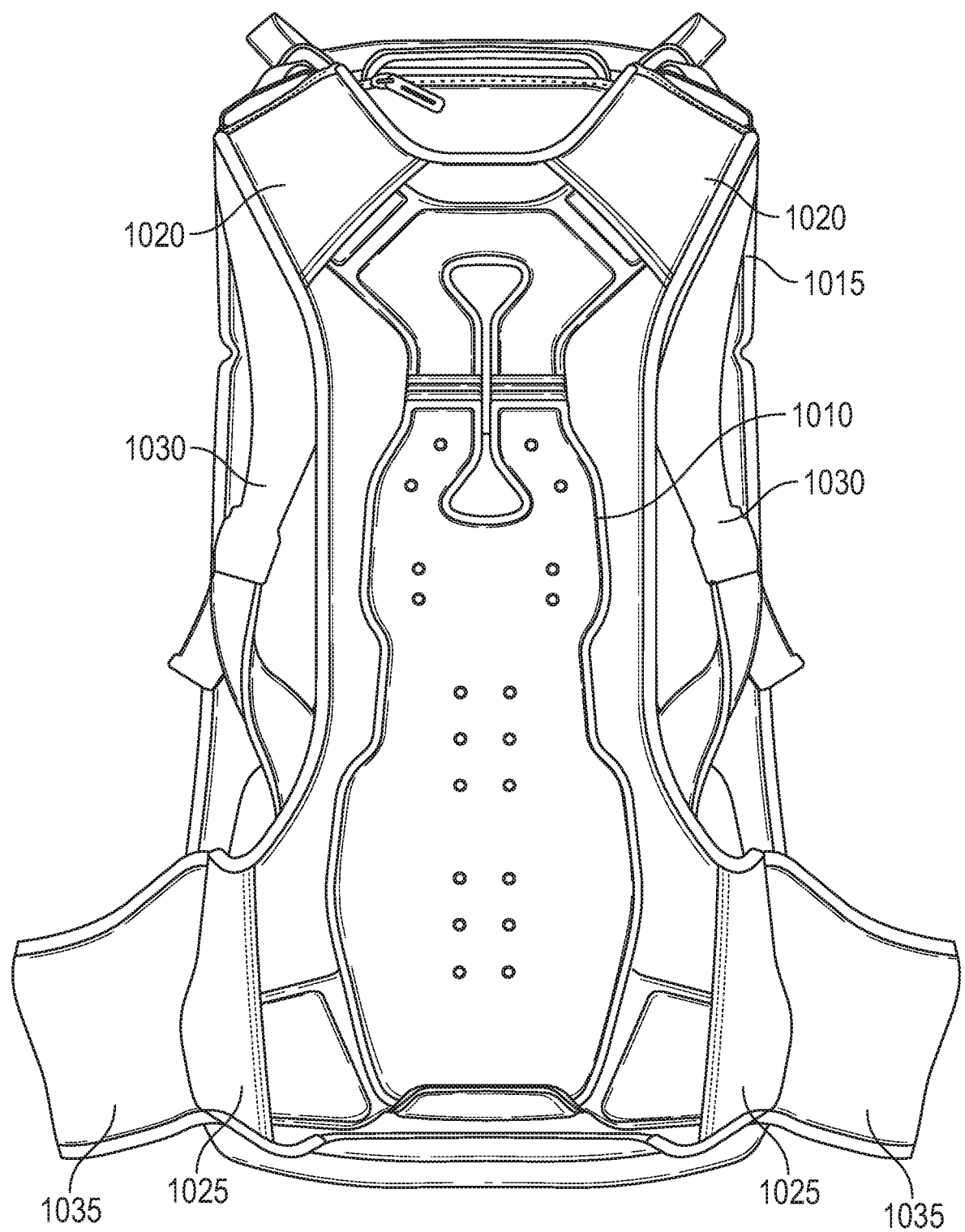
FIG. 10 is a front elevation view of a system attached to a backpack according to an example embodiment.

FIG. 10 is a front elevation view of system 1010 attached to a backpack 1015. Backpack 1015 includes shoulder pockets 1020 which are shaped to fit over shoulder wrap portions 136. Waist pockets 1025 are shaped to fit over waist wrap portions 138. The pairs of pockets 1020 and 1025 engage and support the system 1010 while the backpack is being worn. Backpack straps 1030 and a backpack belt 1035 may be used to secure the backpack and system to the back of a wearer.

Figure 11:
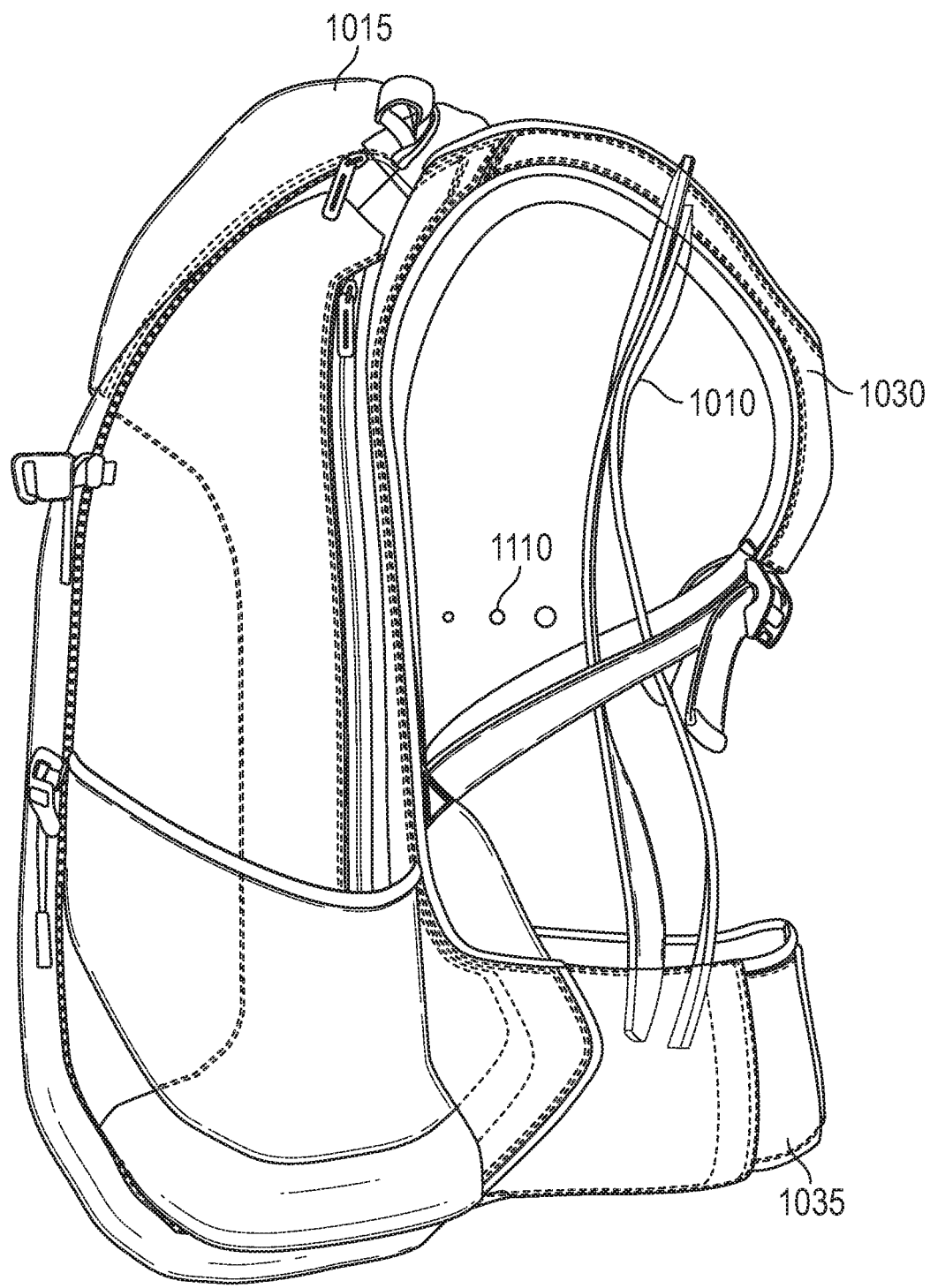
FIG. 11 is a side elevation view of the backpack of FIG. 10 with the system shown unattached.

FIG. 11 is a side elevation view of the backpack 1015 with system 1010 shown unattached. Dots 1110 indicate the direction the system 1010 is moved to be attached to the pockets of the backpack 1015. The backpack may include multiple different zipper pockets and other features of backpacks, with the system 1010 essential operating as an internal frame that provides back support.

Figure 12:
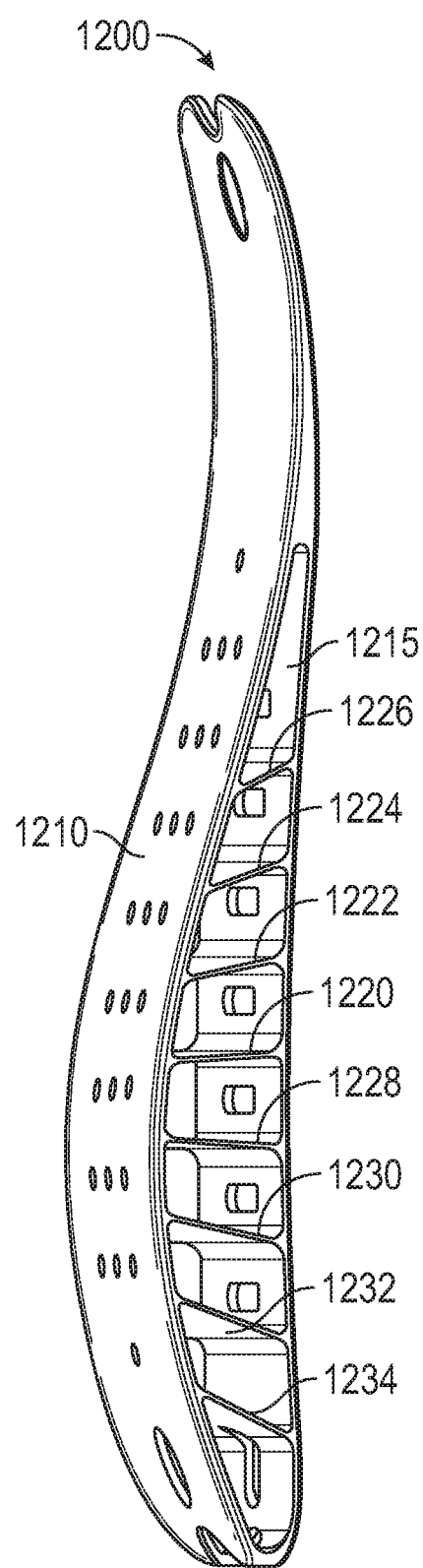
FIG. 12 is a perspective front view of an alternative artificial spine or back support system having a flexible support and brace portion with stabilizing structures according to an example embodiment.
Figure 13:
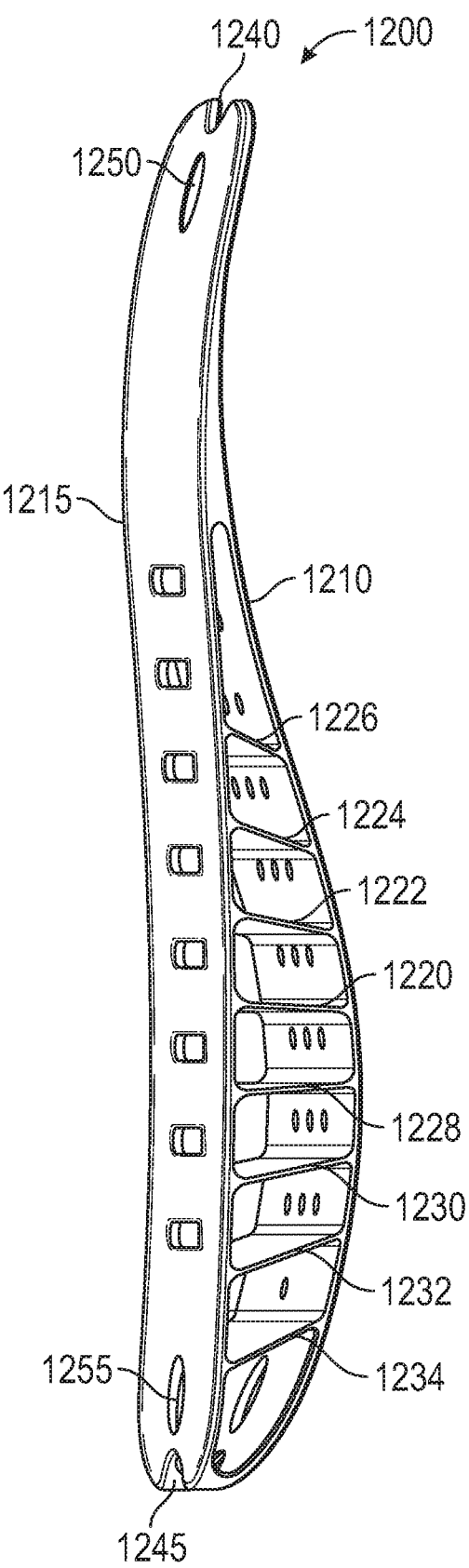
FIG. 13 is a perspective back view of the alternative back support system of FIG. 12.

FIG. 12 is a perspective front view of an alternative artificial spine or back support system 1200 having an "S" shaped flexible support 1210 and brace portion 1215, with stabilizing structures or ribs indicated at 1220, 1222, 1224, 1226, 1228, 1230, 1232, and 1234. In one embodiment, the flexible support 1210 and brace portion 1215 may be formed as described in previous embodiments from similar materials, such as various polymers, which may be injection molded into a single piece. FIG. 13 is a perspective back view of the alternative back support system 1200 having reference numbers consistent with those in FIG. 12.

In one embodiment, the "S" shape corresponds to the shape of normal or average human spine, extending a length of the spine corresponding to different numbers of vertebrae, such as S1 or below, up to below the neck, allowing for free movement of the neck. In one embodiment, the back support system 1200 extends a length corresponding to substantially all of the lumbar curve and thoracic curve. In some embodiments, the back support system 1200 may extend below the lumbar curve into some or all of the sacral curve to provide support for the L5-S1 interface, and in some embodiments may extend above the thoracic curve. In still further embodiments, the length and shape may be varied to fit individual wearers, whose spinal curves may be different lengths and shapes. In still further embodiments, the back support system 1200 may be shaped to provide therapeutic benefits to encourage the wearer's spine to conform to a desired shape consistent with the shape of the back support system 1200.

The flexible support 1210 forms a spring and is adapted to be positioned adjacent a spine of a wearer, support extending along the spine of the wearer when worn. The brace portion 1215 is positioned separated from the flexible support a distance from the spine of the wearer. The stabilizing structures comprise one or more ribs that extend between the flexible support 1210 and brace portion 1215, connecting them together and providing lateral stability between flexible support 1210 and the brace portion 1215 such that their movement is restricted toward and away from the wearer as opposed to toward the sides of the wearer.

In one embodiment, rib 1220 is a center rib that is positioned about half way between a top and bottom of the flexible support 1210 and brace portion 1215 and extends substantially orthogonal to the brace portion 1215 toward the flexible support 1210, contacting the flexible support 1210 at an angle which may not be orthogonal depending on the natural curvature of the spine at the point the rib contacts the flexible support when the flexible support follows the curvature of the spine. Additional ribs may be included, and in one embodiment, the ribs above the center rib as indicated at 1222, 1224, and 1226 progressively slant upward from the flexible support 1210 toward the brace portion 1215. Rib 1222 slants upward the least number of degrees from orthogonal, while rib 1226 slants upward the most. The maximum slant may be about 25 degrees in one embodiment, but may range between 10 and 40 degrees in various embodiments, and even more or less in further embodiments. In one embodiment, multiple ribs may extend substantially orthogonal to the brace portion 1215. The term "substantially orthogonal" may mean equal to a 90 degree angle, or within zero to 10 degrees of the 90 degree angle in further embodiments.

Ribs below the center rib 1220 as indicated at 1228, 1230, and 1232 progressively slant downward from the flexible support 1210 toward the brace portion 1215. Rib 1228 slants downward the least number of degrees from orthogonal, while rib 1232 slants downward the most. The degree of slant may be similar to that of the upward slanting ribs or different in various embodiments.

As the wearer bends forward, the back support device system 1200 follows the movement of the wearer and the flexible support 1210 bends forward with the user's spine. As the flexible support 1210 bends forward, the ribs bend inward as pressure is applied from the flexible support 1210 towards the brace portion 1215. The ribs may deform in an arc in some embodiments or may accordion in others. The ribs being attached to the brace portion 1215 pull and push the brace portion 1215 to follow the movement of the flexible support 1210.

When tension is reduced from the flexible support 1215 (by the wearer's movement), the ribs flex and return to their original position pushing the brace portion 1215 to also return to its original vertical position separated from the flexible portion.

When equally distributed pressure/tension is applied to the flexible support 1210 and brace portion 1215 in their original upright vertical position, the ribs will support the applied pressure evenly. One example of such equally distributed pressure or tension includes when a wearer reclines on the backrest of a chair. The ribs supporting the equally distributed pressure/tension applied will allow the flexible portion 1210, and correspondingly, the wearer's spine, to maintain their original shape. The equally distributed pressure or tension applied directly to the flexible support 1210 and ribs will cause minor movement to the brace portion 1215 away from the flexible support 1210.

As with prior embodiments, the support system 1200 may be inserted into any garment or article of clothing. In one embodiment, a top notches 1240 and bottom notches 1245 in both the flexible support 1210 and brace portion 1215 allow the back support system 1200 to be positioned in place and connected to corresponding attachments in any garment or article of clothing. The notches may also be used to support mounted fixtures holding tension wires. A top opening 1250 and bottom opening 1255 in both the flexible support 1210 and brace portion 1215 further facilitate placement and securing the back support system 1200 within a garment.

The ribs, flexible support 1210 and brace portion 1215 may be formed of the same or different durometer material to allow flexibility and support of the back support system 1200 to resist or allow bending motion of the back support system 1200. In one embodiment, the back support system 1200 may be injection molded into a single piece. As the back support system 1200 conforms to the movement applied, it will push the flexible support 1215 harder into a back of the wearer when the wearer bends.

Figure 14:
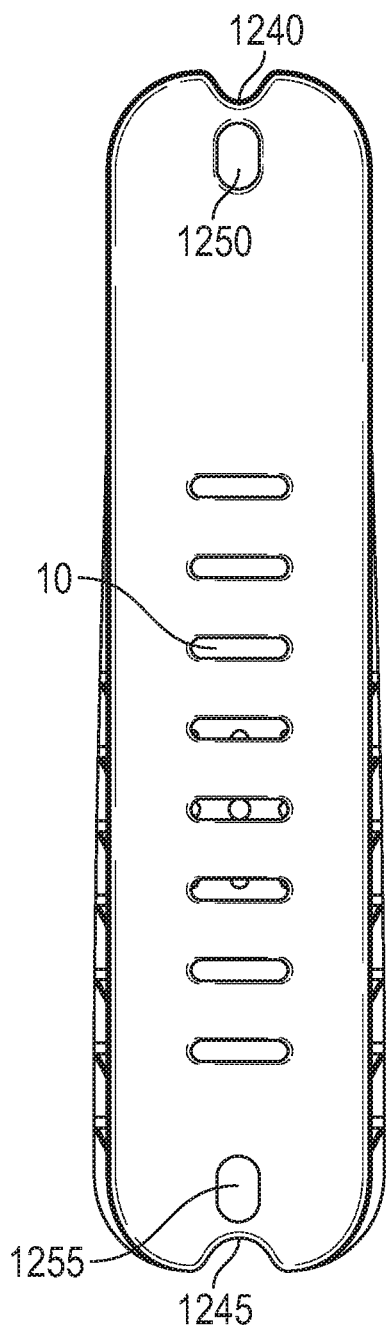
FIG. 14 is a back elevational view of the back support system of FIG. 12 according to an example embodiment
Figure 15:
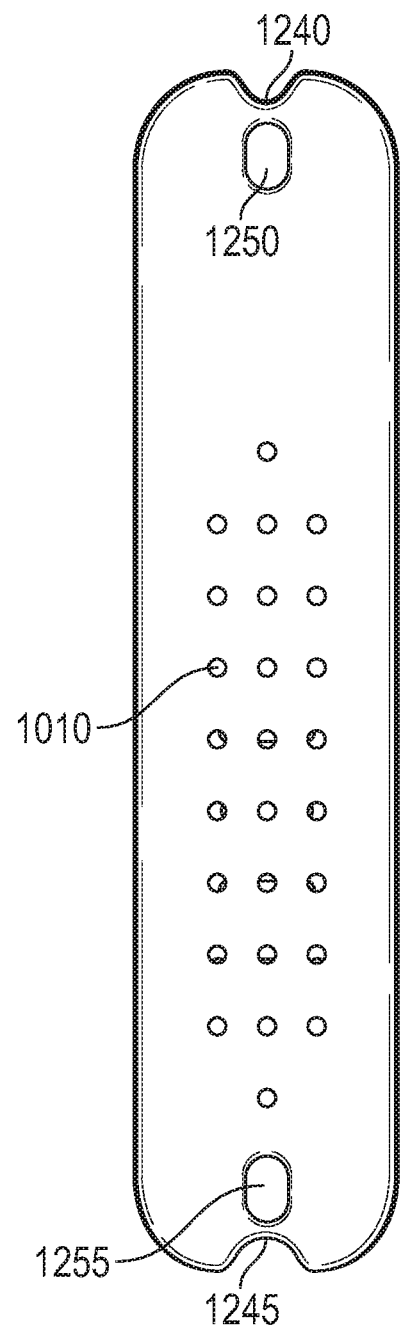
FIG. 15 is a front elevational view of the back support system of FIG. 12 according to an example embodiment.

FIG. 14 is a back elevational view of the back support system 1200 according to an example embodiment, and FIG. 15 is a front elevational view. Openings 910 and 1010 allow airflow to pass through the brace portion 1215 and flexible support 1210 respectively, even when incorporated into a garment. These openings can be of any pattern or design in various embodiments suitable for providing such airflow, yet not so numerous or large as to interfere with the functioning on the flexible support 1210 and brace portion 1215.

Figure 16:
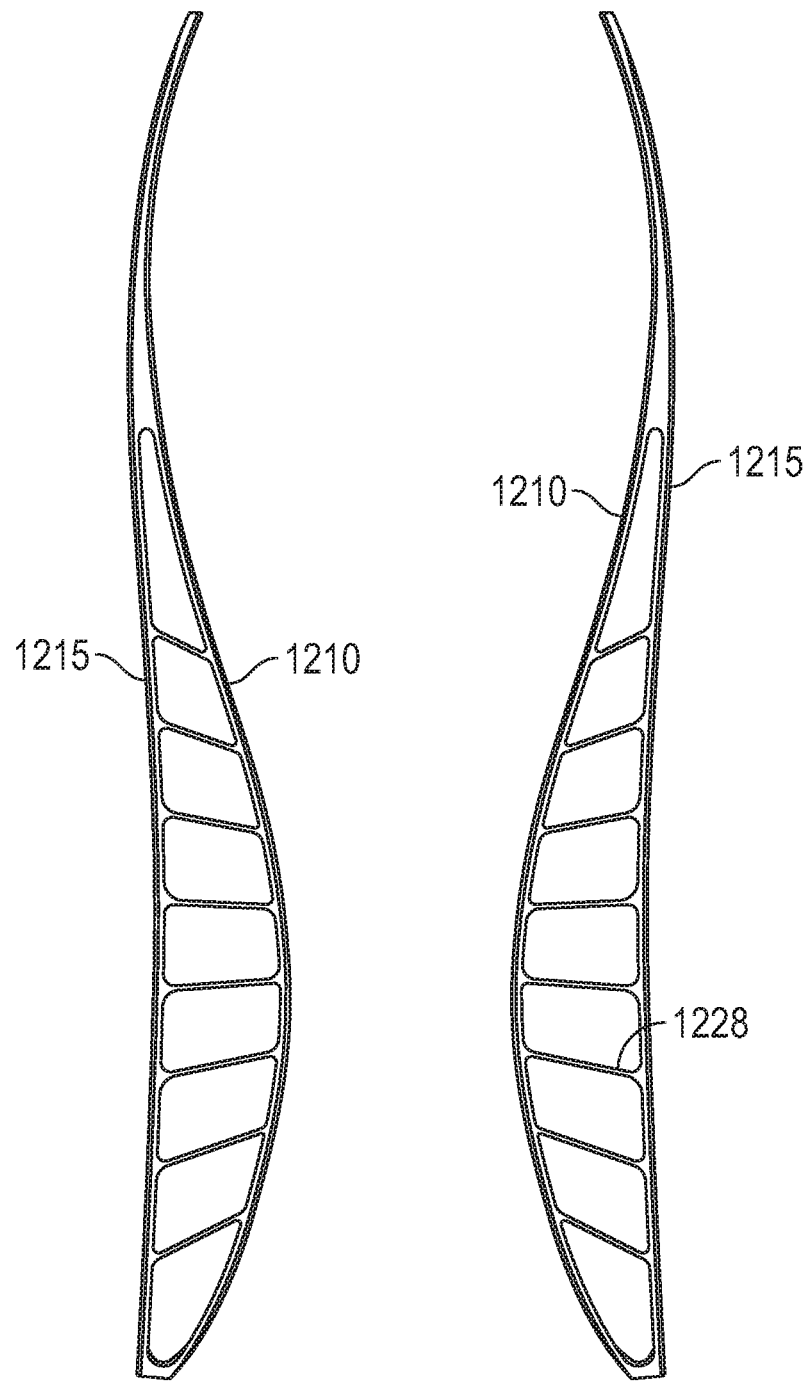
FIG. 16 is a right elevational view of the back support system of FIG. 12 according to an example embodiment.
Figure 17:
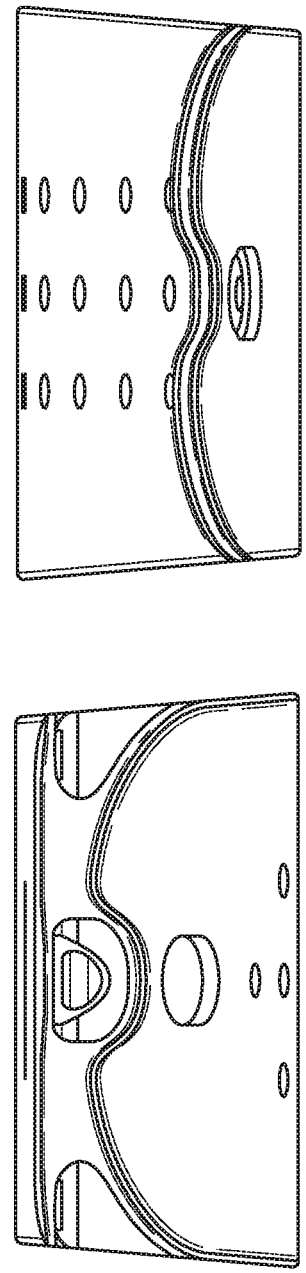
FIG. 17 is a left elevational view of the back support system of FIG. 12 according to an example embodiment.

FIG. 16 is a right elevational view, and FIG. 17 is a left elevational view of the back support system 1200 according to an example embodiment. FIGS. 16 and 17 illustrate the positioning of the fins in further detail. Note also, that from the previous perspective views, the fins may extend laterally along a width of the flexible support 1210 and brace portion 1215. Such extension provides maximum lateral support for preventing opposing lateral movement of the flexible support 1210 and brace portion 1215, resulting in a more stable back support system 1200. In further embodiments, the ribs need not extend along the entire width of the flexible support 1210 and brace portion 1215, and may even include different arrangements of beams and other structures useful in inhibiting lateral movement of the flexible support 1210 and brace portion 1215 in different directions.

A method of wearing a back support device includes placing the flexible support 1210 adjacent a spine of a wearer such that the flexible support 1210 extends along the spine of the wearer when worn. The brace portion 1215 or plate has two ends that are coupled to two ends of the flexible support. The brace plate defines a portion that extends directly between one coupled end to the other coupled end, and wherein the portion is positioned behind and is spaced from the flexible spring support by the ribs.

In one embodiment, the method further includes integrating the support system 1200 into a garment.

Figure 18:
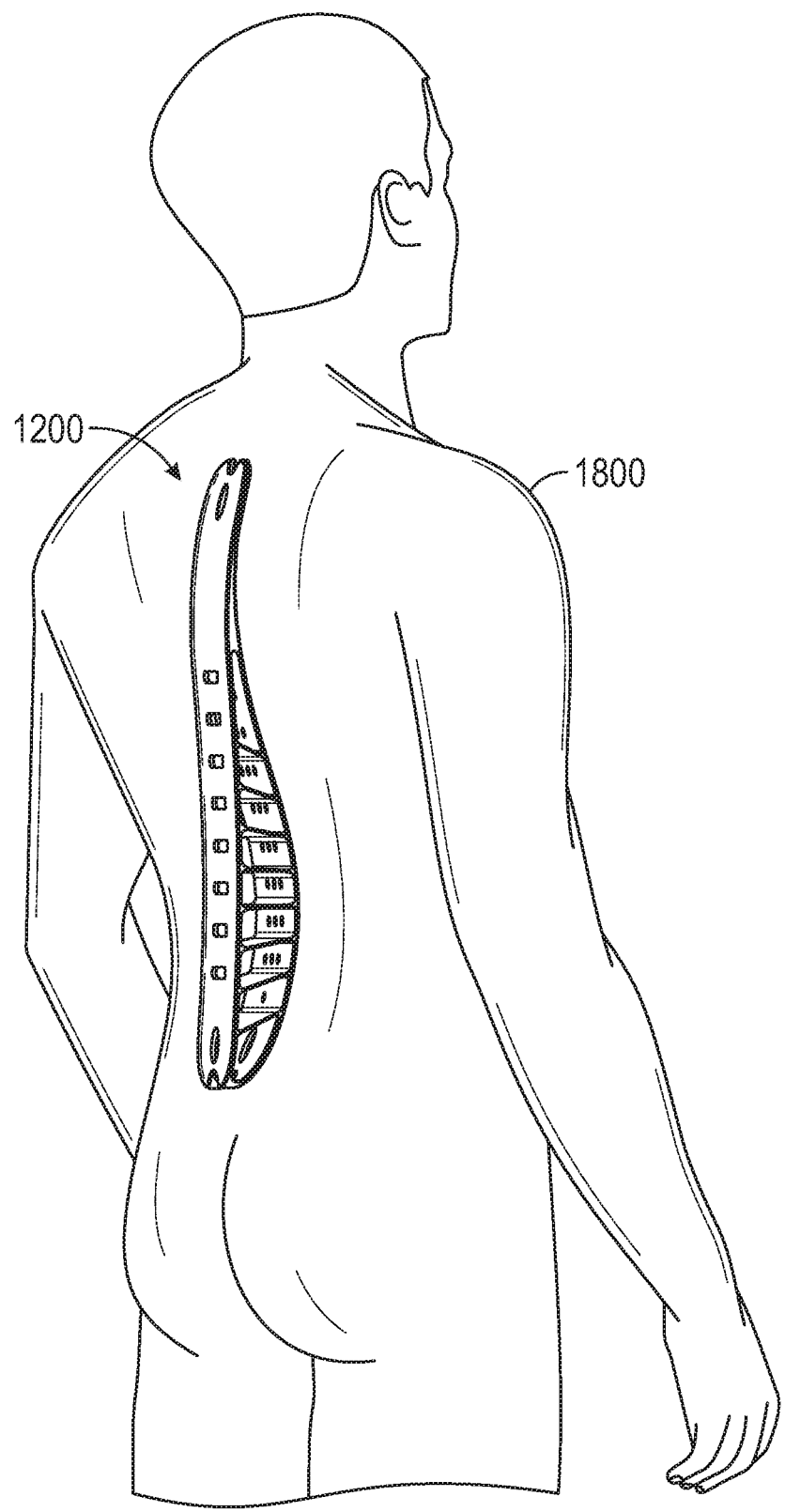
FIG. 18 is a perspective view of back support system of FIG. 12 being worn by a user according to an example embodiment.

FIG. 18 is a perspective view of back support system 1200 being worn by a user 1800 according to an example embodiment.

Figure 19:
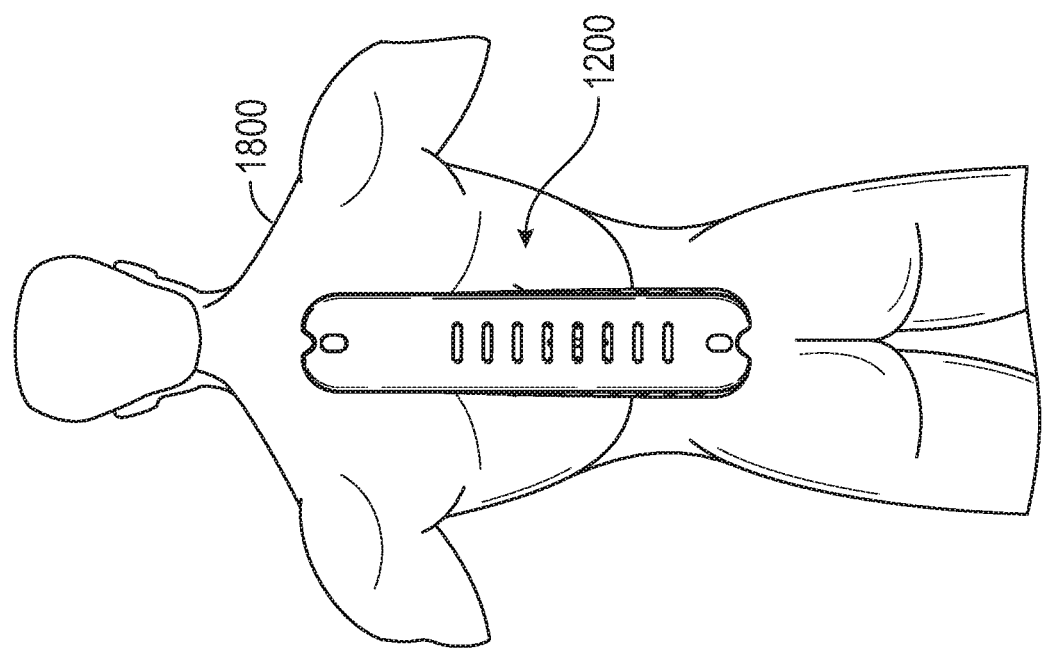
FIG. 19 is a back view of back support system of FIG. 12 being worn by a user according to an example embodiment.

FIG. 19 is a back view of back support system 1200 being worn by user 1800.

Figure 20:
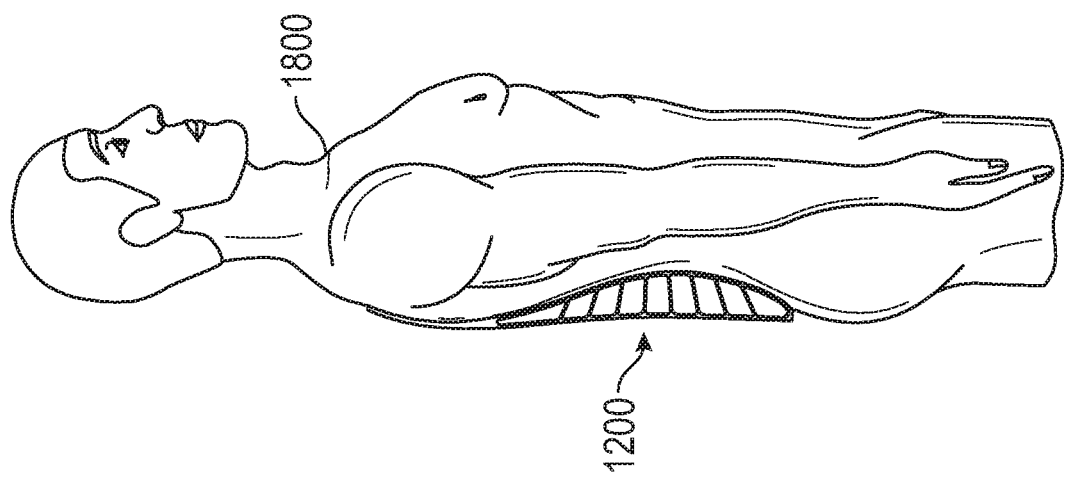
FIG. 20 is a side view of back support system of FIG. 12 being worn by a user according to an example embodiment.

FIG. 20 is a side view of back support system 1200 being worn by user 1800.

Figure 21:
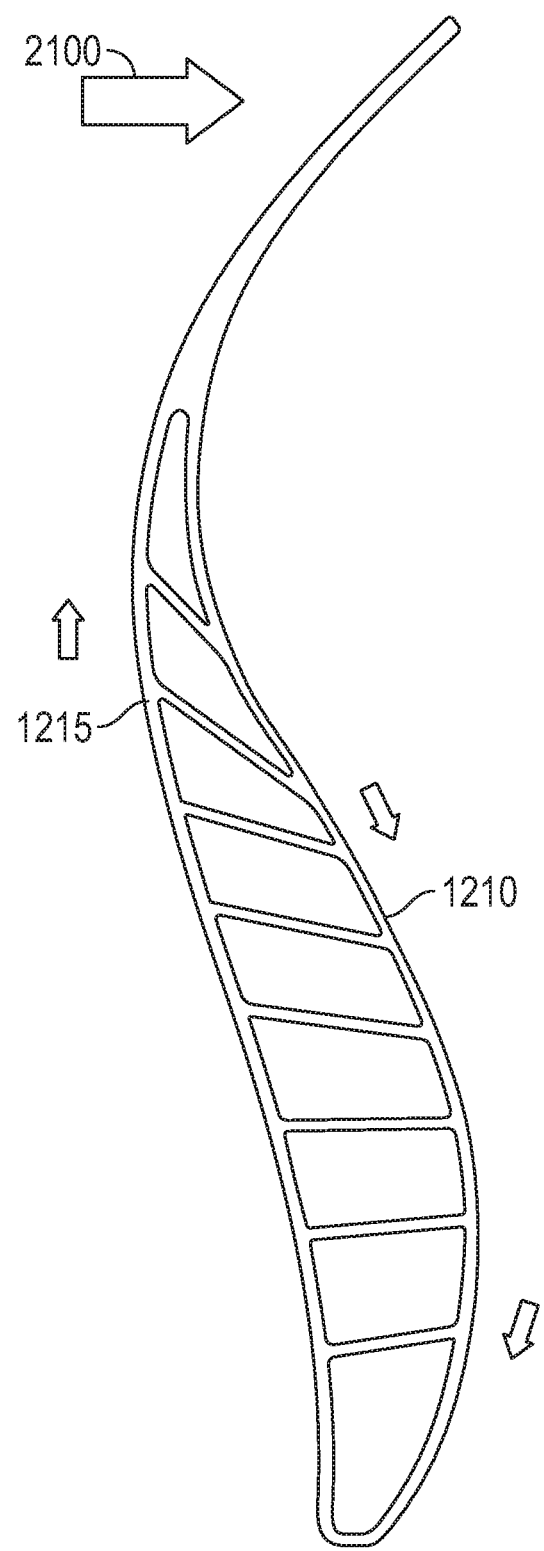
FIG. 21 is a right elevational view of back support system of FIG. 12 illustrating a change in shape of the back support system responsive to a wearer bending forward according to an example embodiment.

FIG. 21 is a right elevational view of back support system 1200 illustrating a change in shape of the back support system 1200 illustrating a change in shape of the back support system responsive to a wearer bending forward as represented by arrow 2100 according to an example embodiment.

Figure 22A:
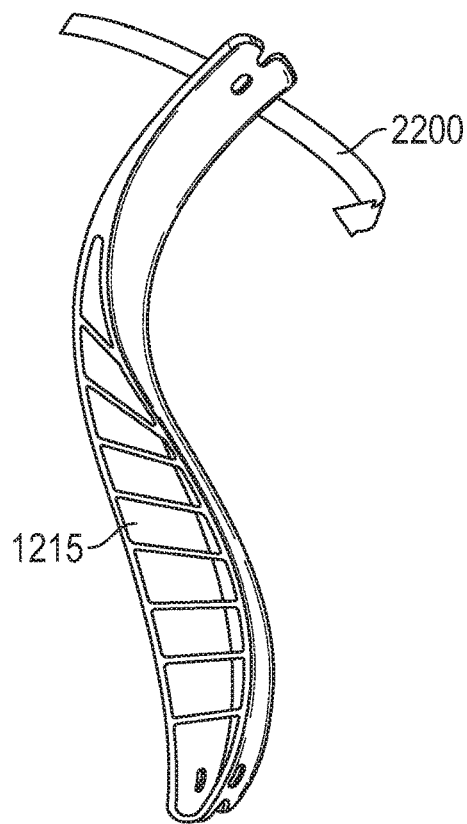
FIG. 22A is a right perspective view of the back support system of FIG. 12 illustrating a change in shape of the back support system responsive to a wearer twisting to the right according to an example embodiment.

FIG. 22A is a right perspective view of the back support system 1200 illustrating a change in shape of the back support system responsive to a wearer twisting to the right as indicated by arrow 2200 according to an example embodiment.

Figure 22B:
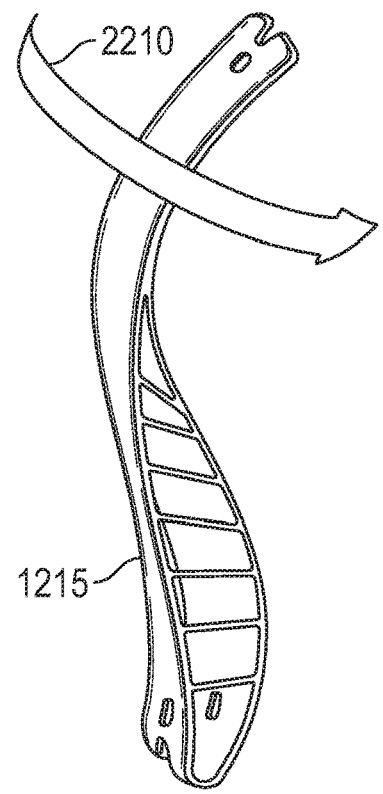
FIG. 22B is a right perspective view of a back support system of FIG. 12 illustrating a change in shape of the back support system responsive to a wearer twisting to the left according to an example embodiment.

FIG. 22B is a right perspective view of a back support system illustrating a change in shape of the back support system responsive to a wearer twisting to the left as indicated by arrow 2210 according to an example embodiment. FIGS. 22A and 22B show lateral movement from side to side to support the wearer's torso movement as the torso twists. Note that the ribs ensure that the flexible support and brace portion move together responsive to twisting and bending of the wearer's torso.

Figure 23:
FIG. 23 is a right side view of a back support system being worn by a wearer bending forward according to an example embodiment.

FIG. 23 is a right side view of a back support system being worn by a wearer bending forward according to an example embodiment. FIGS. 21, 22A, 22B, and 23 show the back support system has forward, backward, and lateral movement mostly on the top half. Similar but less movement may occur towards the bottom half, mostly as a response to the upper half.

Building the back support device into a garment makes it ready and available to use. Having the device adjustable, the wearer can comfortably use it when lifting heavy loads and when sitting and walking. The flexible support creates pressure on the lower back muscles encouraging the user to lock their back to limit their range of motion and prevent hyperextension.

The back support device can be removable for replacement and for keeping the garment washable. In one embodiment, a body fluid-repellent fabric coating protects the life of the uniform from normal use. The back support system and garment can both have an athletic fit for elasticity, efficiency, and breathability. In one embodiment, the portions 110 and 115 form a combination of two plates with spine-lacing 130, 140, 155 support that provides an efficient design to create rigidity, adjustability, and flexibility for back support. In a further embodiment, an adjustable back brace/spring with a belt and shoulder straps can be worn at home over any article of clothing. Another version is a robust back brace with artificial spine/spring with padding on the straps for users who are lifting all day, with extra support around the waist.

In professional use, a heavy-duty back brace with artificial spine/spring may be built into law enforcement, fire, and EMT uniforms, among other professional needs.

An example of how the back support unit could be built into a garment is best demonstrated through an EMT uniform. The built-in adjustable back brace and flexible support for back support could be inserted into a paramedic uniform. The system in one embodiment is designed to be worn throughout the duration of a response call. It is also suggested to be worn during the time the EMT is at the station, as maintenance around the vehicle may require heavy lifting. Some EMT Paramedics average 48 hour shifts, and emergency calls can each last for several hours increasing back and muscle fatigue and jeopardizing correct posture.

The back support device can be adjusted to loosen the fit when the paramedic is not directly using the shirt/uniform (example: driving the ambulance) and tightened right before the time of heavy lifting.

As the EMT bends over to lift, the back brace automatically adjusts following the shape of the lumbar spine, assisting the EMT in tightening their lower back muscles, by adding the needed pressure to the lower back. With this built-in back brace and artificial spine (spring), EMTs can safely lift and transport patients and other heavy loads their jobs require.

Example Materials:

The majority of a uniform may be made of bamboo fibers for abrasion resistance and durability. Other fibers providing suitable stiffness and durability may be used in further embodiments. The side panels underneath the arms may be made of Lycra or other materials. The entire uniform may optionally be sprayed with a repellant for protection against body fluids.

The artificial spine may be formed with a low density polyethylene (LDPE 54D) strip, and a high density polyethylene (HDPE 70D) strip. Other materials that may be used include but are not limited to carbon fiber, Kevlar, and Nylon, and (ABS) Acrylonitrile butadiene Styrene. Reflective piping may be placed on the shoulders and side panels for light reflection.

Two plastic turn dials, with a polypropylene or metal wire, wrap around the torso and connect to the back brace portion and flexible support. Foam padding may be stitched on the inside of the back brace and flexible support for comfort.

Technical Specs and Production Method:

The pattern of the uniform may be cut out from different materials and stitched together. A top and a bottom pocket may be added along the center of the back to allow the flexible support and brace portion to slip in and out. The pattern may follow average male, female, and children sizes. The back brace and flexible support may be cut from polyethylene strips. The strips are then bent to the natural "S" shape of the lumbar and secured together using round rivets or other suitable fasteners, such as adhesives, clamps, etc. The side garments are cut to their exact shape and laced together using the wire. The back brace and flexible support forming the artificial spine may be inserted into pockets along the center of the back, and the wire is run through the inside of the uniform to connect to the turn dials in the front.

In a further embodiment, A back support device includes one or more lateral stability supports to reduce potential lateral movement between the flexible support and brace portion of the back support device.

Figure 24:
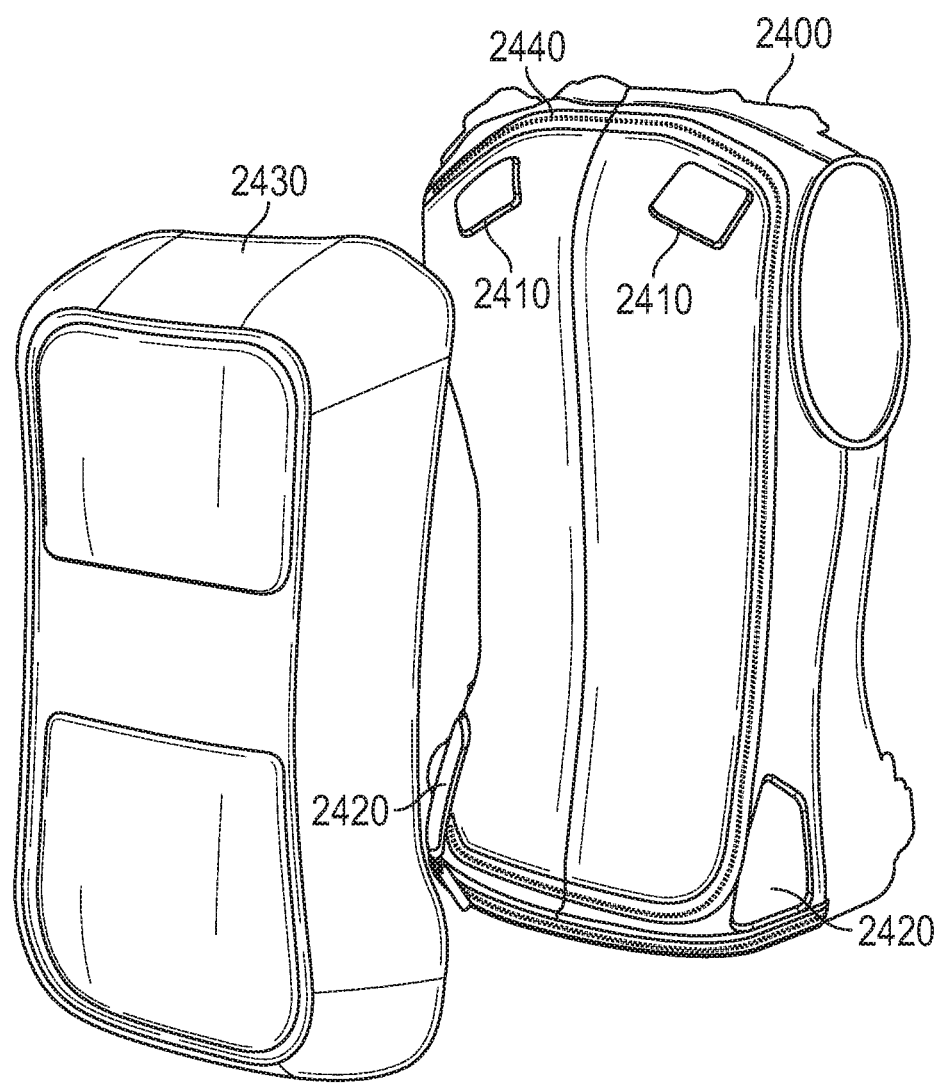
FIG. 24 is a perspective view of a garment for use with one or more support systems according to an example embodiment.

FIG. 24 is a perspective view of a garment 2400 for use with one or more support systems, such as support system 100. The garment may be in the shape of a utility vest or jacket with multiple hook and loop attachment points for a support system having mating hook and loop attachment points. Top attachment points 2410 are positioned to attach to attachment points on the shoulder wrap portions 136 of the system, and bottom attachment points 2420 are positioned to attach to attachment points on the waist wrap portions 138. Garment 2400 may also include a detachable bag 2430 that may be attached to the garment 2400 via a wrap around zipper 2440. The bag 2430 may be attached to the garment 2400 with or without a support system.

Figure 25:
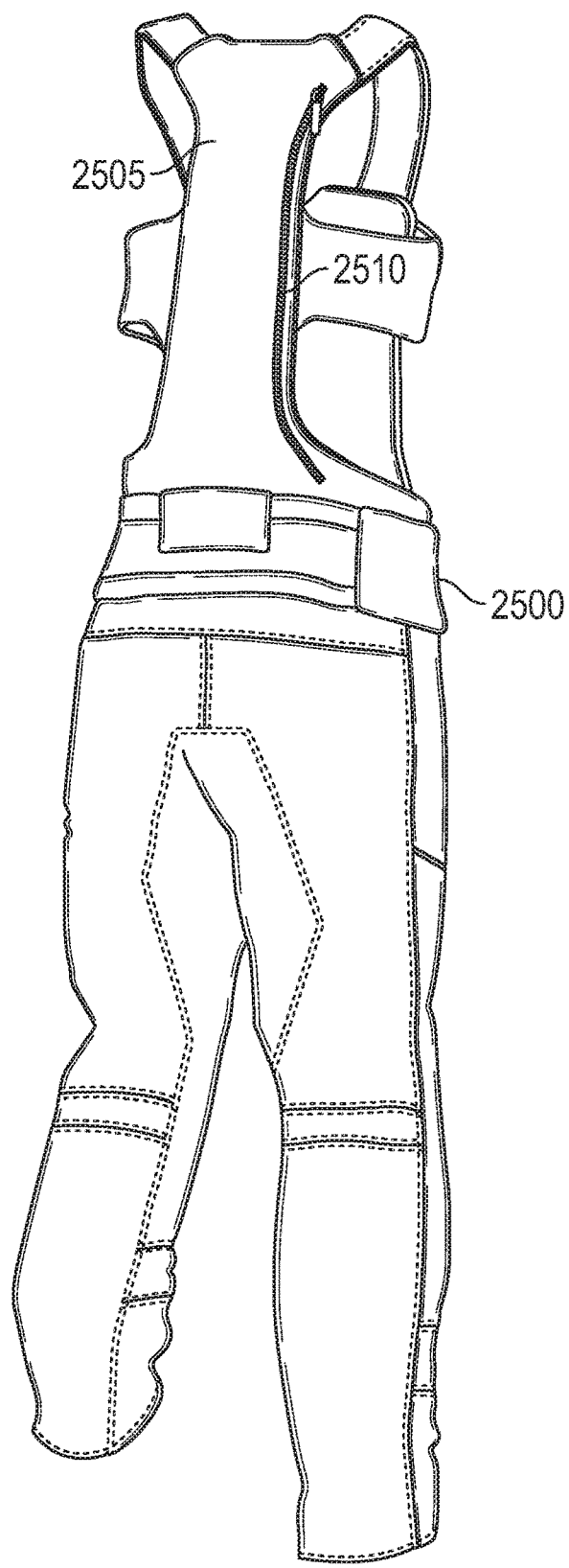
FIG. 25 is a perspective view of a garment 2500 for use with one or more support systems according to an example embodiment.

FIG. 25 is a perspective view of a garment 2500 for use with one or more support systems, such as support system 1200. Garment 2500 may be a in the form of overall style pants in one embodiment. The back of the garment 2500 includes a pocket 2505 shaped to fit a support system such as support system 1200. A zipper 2510 may be used to close the pocket 2505 around system 1200 such that system 1200 provides back support while the garment 2500 is worn.

Figure 26:
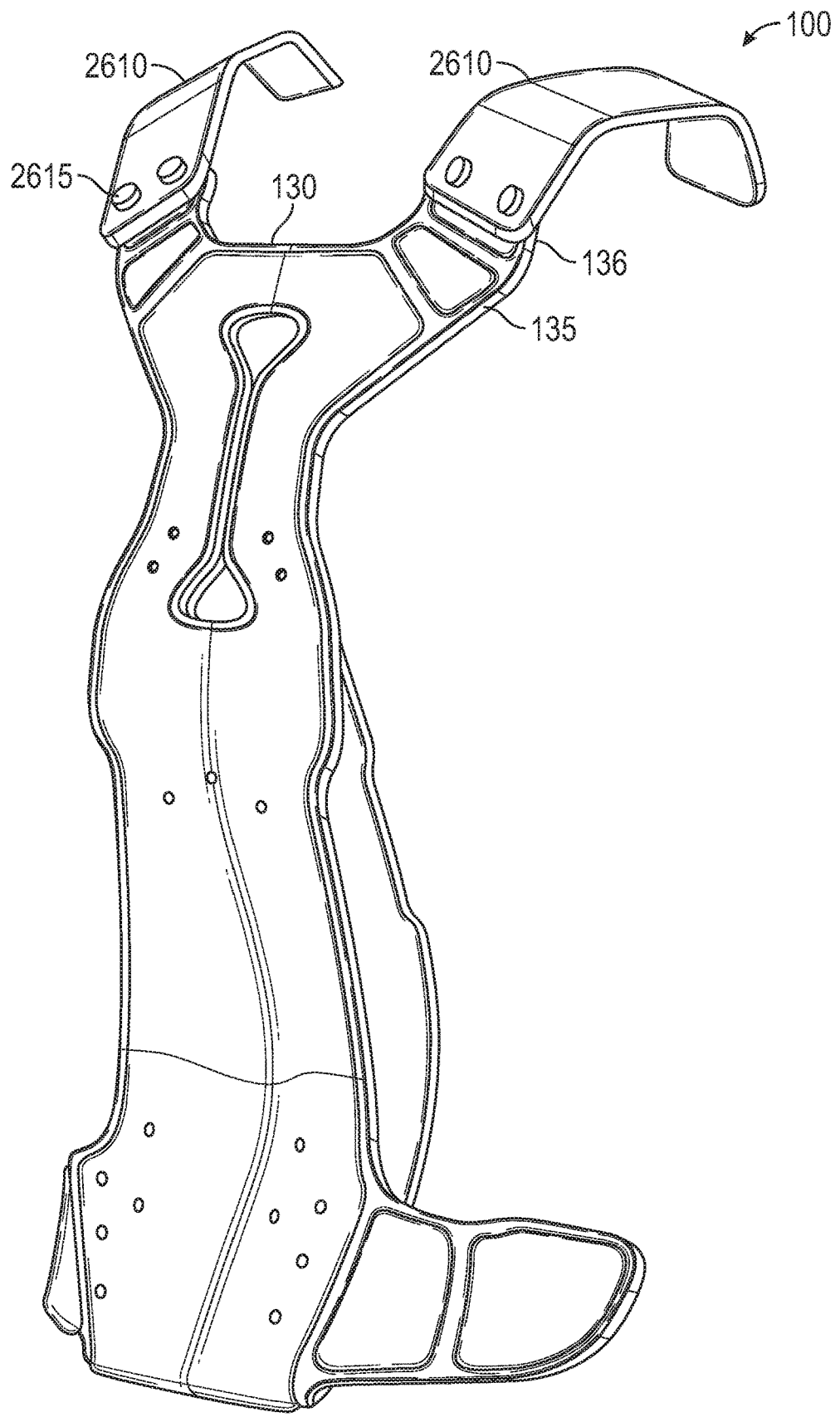
FIG. 26 is a perspective view of support system with the inclusion of shoulder hooks attached via fasteners to shoulder wrap portions according to an example embodiment.

FIG. 26 is a perspective view of support system 100 with the inclusion of shoulder hooks 2610 attached via fasteners 2615 to shoulder wrap portions 136. The shoulder hooks 2610 may be formed of a rigid material to extend over the shoulders of wearer to maintain the system 100 in position on the wearer.

Figure 27:
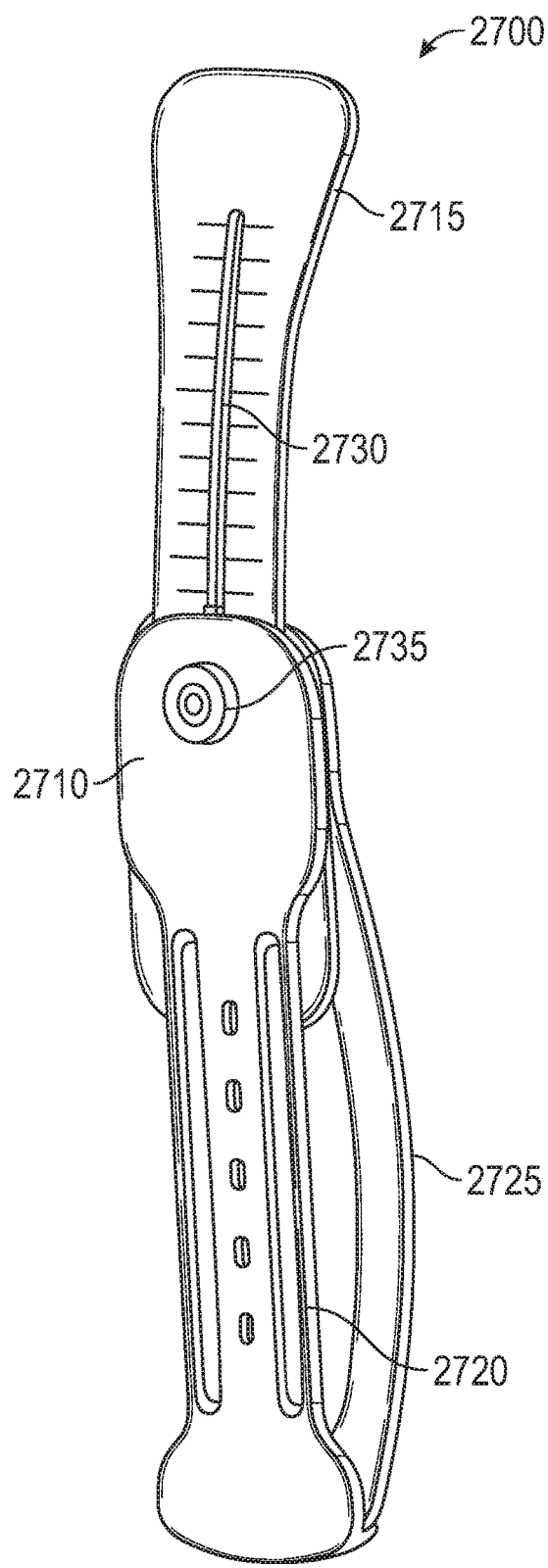
FIG. 27 is a perspective view of an adjustable support system according to an example embodiment.

FIG. 27 is a perspective view of an adjustable support system 2700. A brace portion 2710 is divided into an upper brace portion 2715 and a lower brace portion 2720. The lower brace portion supports a flexible arc 2725. The upper brace portion 2715 includes a channel 2730 along a portion of a vertical length of the upper brace portion. The lower brace portion 2720 includes a fastener 2735 that extends through the channel 2730 and couples the upper brace portion 2715 to the lower brace portion 2720 when tightened. Loosening the fastener 2735 allows the upper brace portion to move and either shorten or lengthen an overall length of the brace portion 2710. A measuring guide may be included on the upper brace portion 2715 to provide a total length. The fastener 2735 may be tightened to secure the upper brace portion and lower brace portion at a desired total length.

Figure 28:
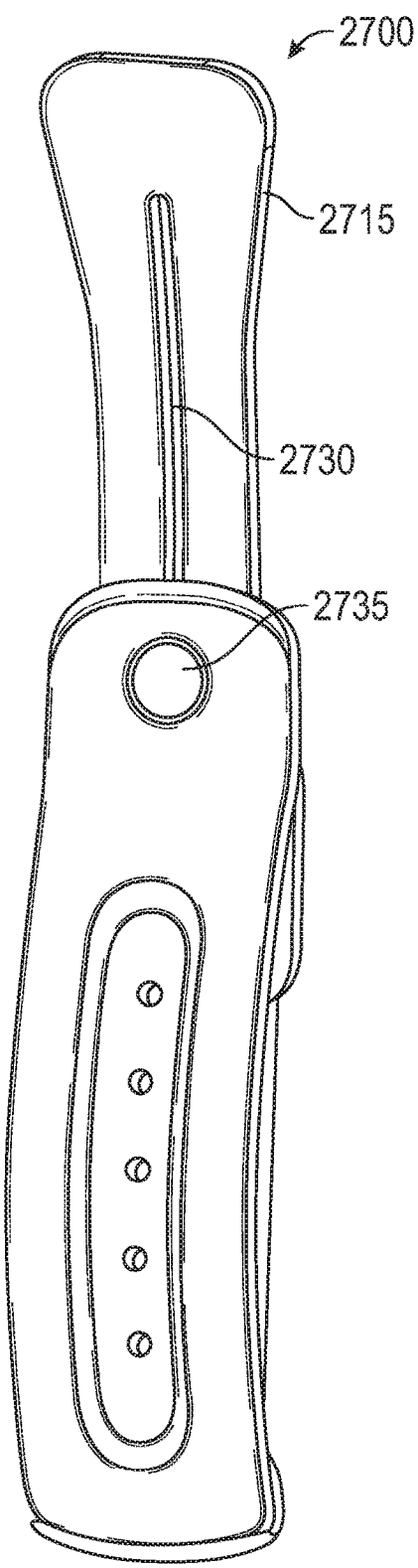
FIG. 28 is a perspective view of the other side of support system of FIG. 27 according to an example embodiment.

FIG. 28 is a perspective view of the other side of support system 2700.

Figure 29:
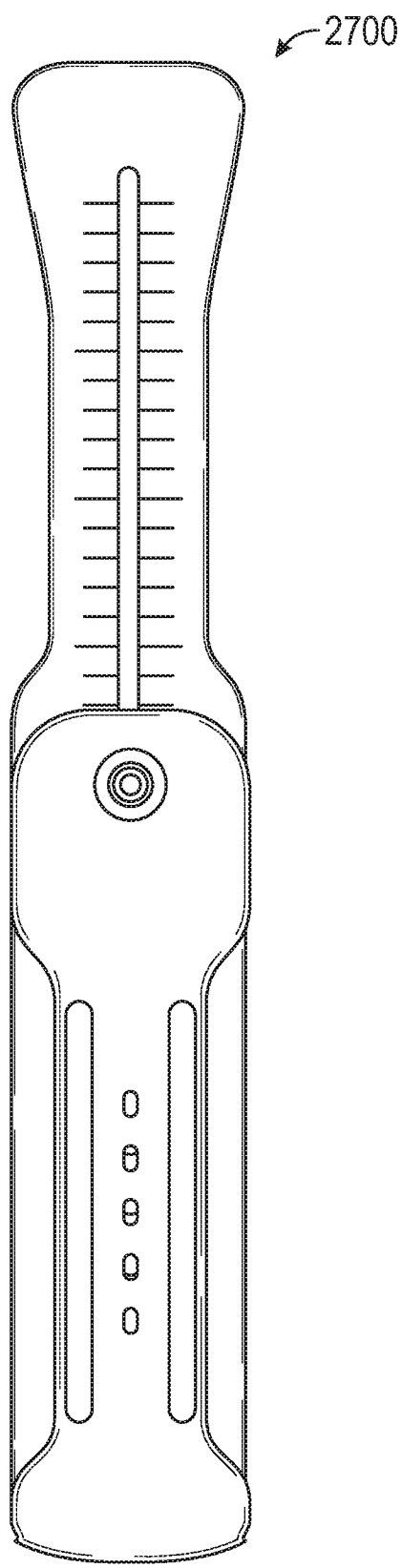
FIG. 29 is a back view of the support system of FIG. 27 according to an example embodiment.

FIG. 29 is a back view of support system 2700.

Figure 30:
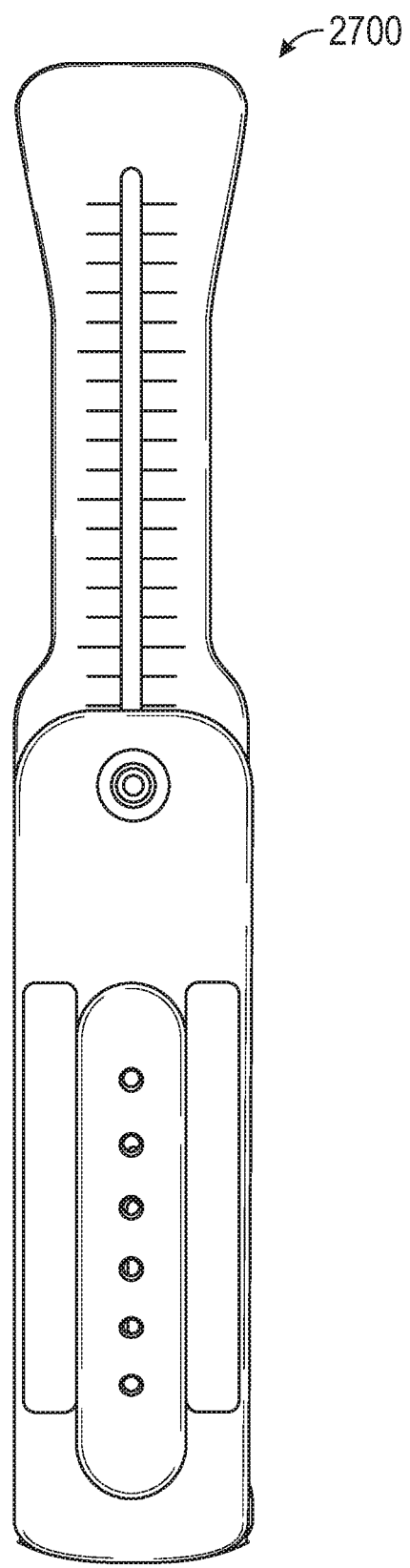
FIG. 30 is a front view of the support system of FIG. 27 according to an example embodiment.

FIG. 30 is a front view of support system 2700.

Figures 31, 32:
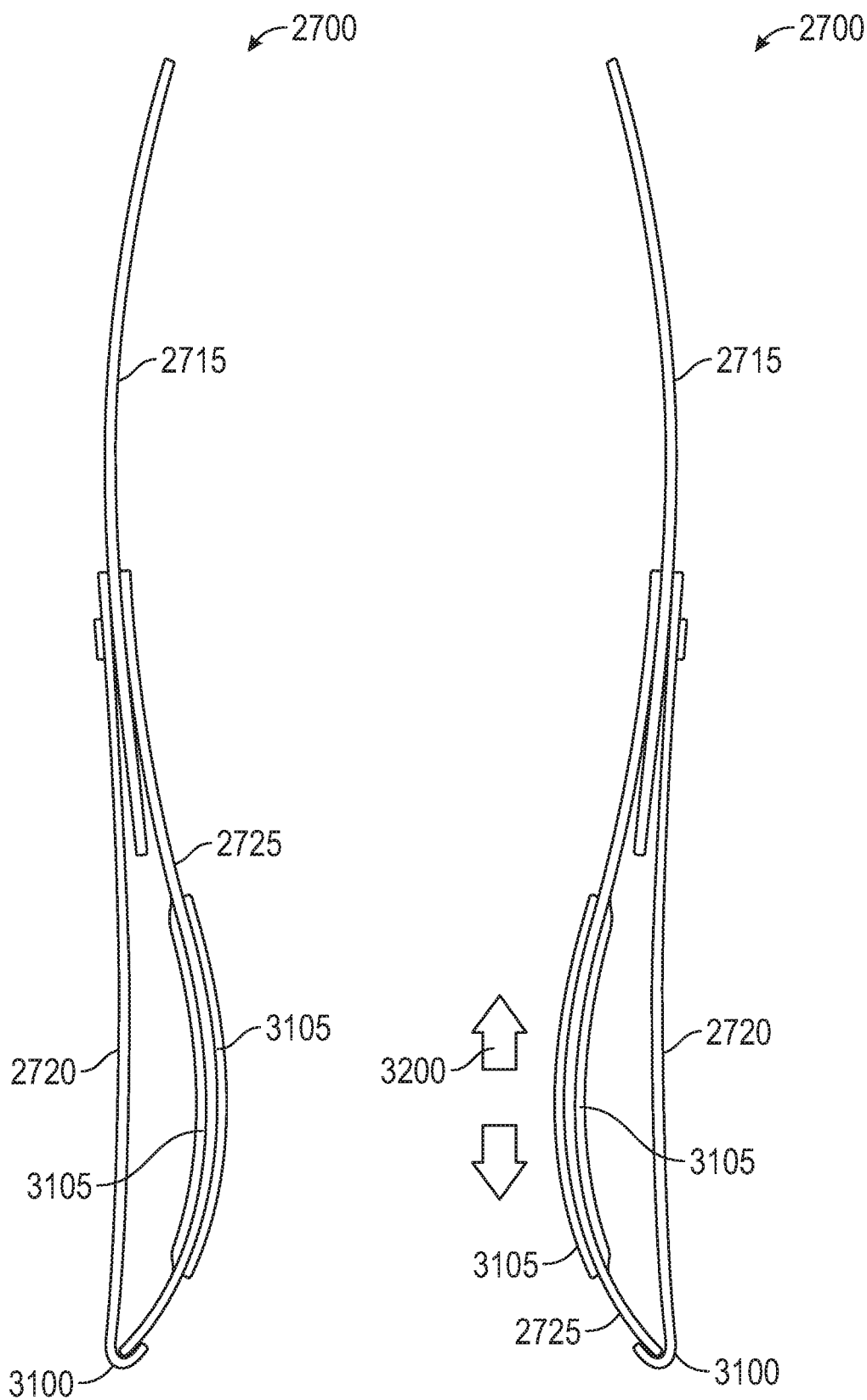
FIG. 31 is a side view of the support system of FIG. 27 according to an example embodiment.
FIG. 32 is a side view of the support system of FIG. 27 according to an example embodiment.

FIG. 31 is a side view of support system 2700. This figure illustrates how the upper brace portion 2715 can slide between the lower brace portion 2720 and the arc 2725. Padding 3105 on the arc 2725 is also illustrated. A lower folded portion or hook 3100 supports the lower end of arc 2725, while the upper end of arc 2725 is attached via fastener 2735, sandwiching the upper brace portion 2715 between arc 2725 and lower brace portion 2720.

FIG. 32 is a side view of support system 2700. Arrows 3200 illustrate that the arc portion 2725, also referred to as a front lumbar part, moves up and down in response to wearer movement.

Figure 33:
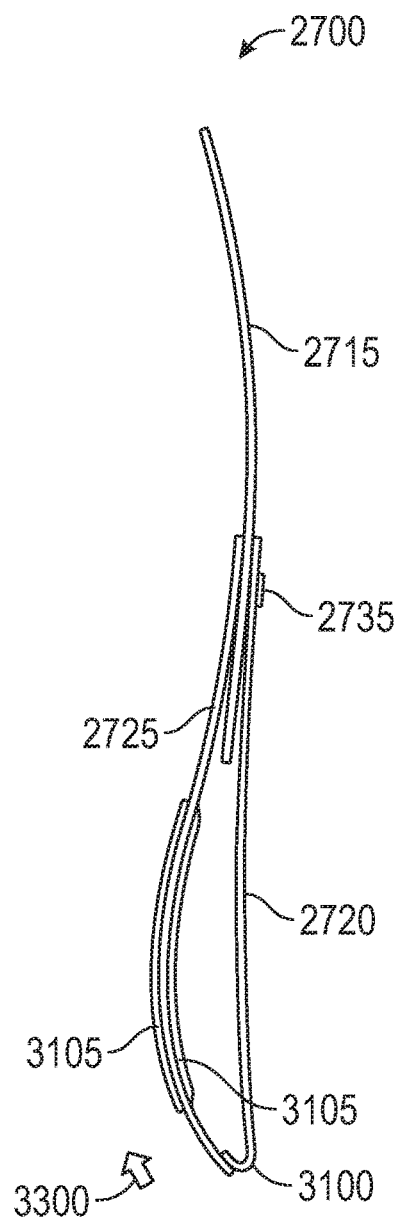
FIG. 33 is a side view of the support system of FIG. 2700 showing movement of an arc portion to release engagement according to an example embodiment.

FIG. 33 is a side view of support system 2700 with an arrow 3300 showing movement of the arc portion 2725 to release engagement with hook 3100. The released arc portion 2725 releases tension on the arc, allowing it to straighten out as illustrated in FIG. 34.

Figure 34:
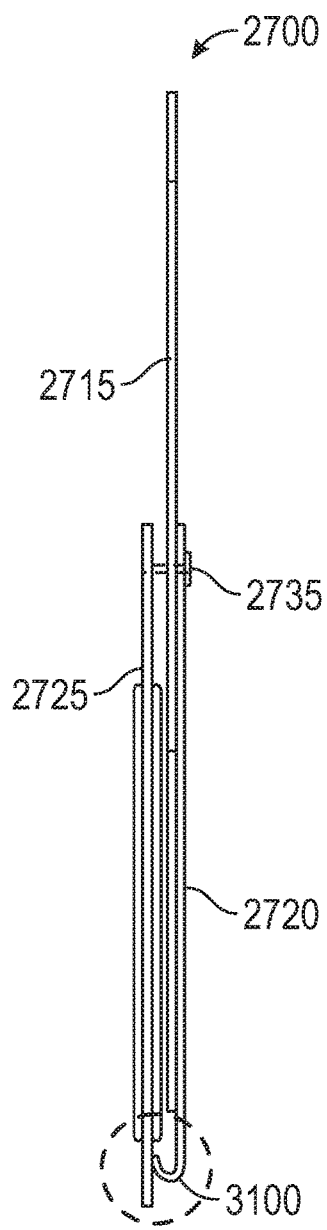
FIG. 34 is a side view of the support system of FIG. 27 showing the support system with the lower brace portion according to an example embodiment.

FIG. 34 is a side view of support system 2700 showing the support system with the lower brace portion 2725 in the released position. The fastener 2735 may be loosened at this point.

Figure 35:
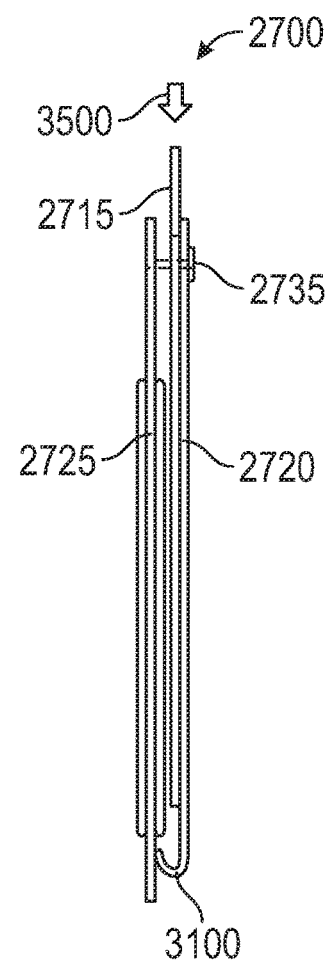
FIG. 35 is a side view of the support system of FIG. 27 with the upper brace portion 2715 slid down between the straightened arc portion 2725 and the lower brace portion 2720 for convenient storage and transport according to an example embodiment.

FIG. 35 is a side view of support system 2700 with the upper brace portion 2715 slid down between the straightened arc portion 2725 and the lower brace portion 2720 for convenient storage and transport.

Figure 36:
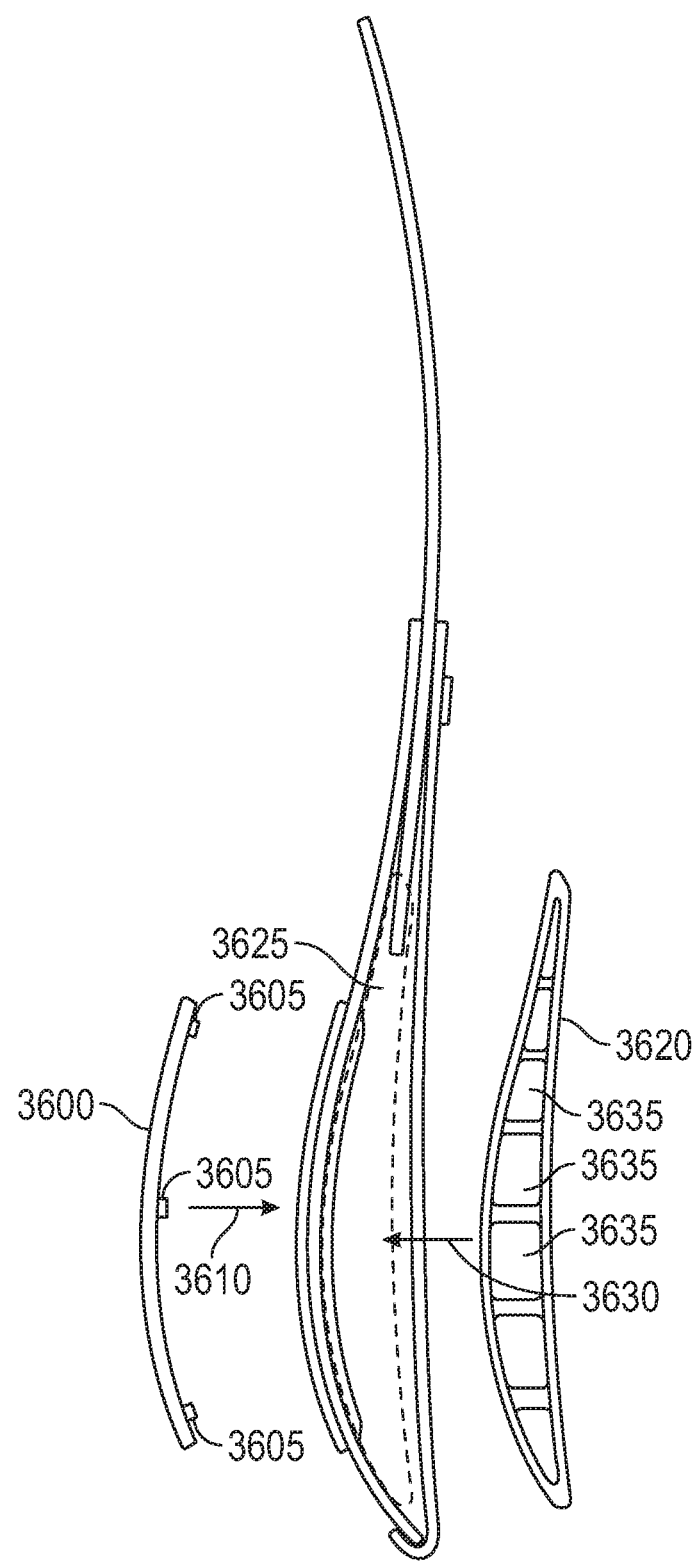
FIG. 36 is an exploded side view of a support system with additional components that can be added for increased comfort and stability according to an example embodiment.

FIG. 36 is an exploded side view of a support system 2700 with additional components that can be added for increased comfort and stability. A detachable front pad 3600 can be formed of soft material and is attachable to the front arc portion 2725 via attachments points referred to as nubs 3605 positioned to securely attach the pad 3600 to the arc via matting openings as indicated by arrow 3610. The pad 3600 may simply removably snap into place. The nubs may be made of a compliant material that bends for insertion and removal yet provides sufficient retentive force to remain in place during use.

A removable inner stabilizer 3620 is similar in construction to support system 1200 and is shaped to fit within an opening 3625 of support system 2700 as indicated by arrow 3630. Stabilizer 3620 may include multiple ribs 3635 to improve stability and enhance the application of force to the spine of the wearer in a desired manner. The ribs 3635 may be horizontal or slanted like the ribs in system 1200.

In further embodiments that stabilizer 3620 may and enclosure sealed on all sides that is filled with fluid and function as an air bag for added comfort. Varying air pressure within the enclosure provides the ability to adjust flexibility of the system 2700. The enclosure and resulting system 2700 will be more flexible with less air but stiffer with more air. Material used may be (TPU) Thermoplastic Polyurethane.

Examples

1. A back support system comprising:
a flexible support formed in the shape of a portion of a spine of a person, the flexible support formed in a shape corresponding to the shape of the spine;
a lower brace portion coupled to the flexible support proximate ends of the flexible support, the brace portion adapted to force the spring portion toward the spine as a wearer bends; and
an upper brace portion adjustably coupled to the lower brace portion for adjusting an overall length of the combined upper and lower brace portions.

2. The back support system of claim 1 and further comprising at least one rib extending between the flexible support and the brace portion.

3. The back support system of claim 2 wherein the at least one rib extends substantially orthogonally from the brace portion toward the flexible support portion near a middle of a length of the brace portion.

4. The back support system of claim 2 wherein the at least one rib extends laterally for substantially an entire width of the brace portion.

5. The back support system of claim 4 wherein the at least one rib extends laterally for substantially an entire width of the flexible support.

6. The back support system of claim 2 wherein the at least one rib comprises multiple ribs, including a center rib that extends substantially orthogonally from the brace portion toward the flexible support portion, a second rib above the center rib that extends at a downward angle from the brace portion toward the flexible support portion, and a third rib below the center rib that extends at an upward angle from the brace portion toward the flexible support portion.

7. The back support system of claim 6 wherein the at least one rib comprises further multiple ribs above the second rib and below the third rib, each rib extending at a larger angle the further such ribs are positioned from the center rib.

8. The back support system of claim 2 wherein the back support system is configured to follow the movement of a wearer as the wearer bends forward such that the flexible support bends forward.

9. The back support system of claim 8 wherein responsive to tension being reduced from the flexible support by the wearer's movement, the at least one rib flexes and returns to its original position, pushing the flexible support to also return to its unstressed position.

10. The back support system of claim 1 and further comprising an adjustable tension wire positioned to extend around a wearer and when tightened, to draw the brace portion towards flexible support, and wherein the adjustable tension wire further includes a tension adjusting control coupled to the wire to releasable tighten the tension wire.

11. The back support system of claim 1 and further comprising a garment having the brace portion and flexible support portion integrated into the garment, and having an upper and a lower lacing integrated into the garment.

12. The back support system of claim 11 and further comprising a pair of respective tightening controls coupled to respective upper and lower lacing and supported by the garment in a position accessible to the wearer to control force on the wearer's spine generated by the brace portion pushing the flexible support portion toward the spine.

13. A back support system comprising:
a flexible support formed in the shape of a portion of a spine of a person, the flexible support extending in an "S" shape corresponding to the shape of the spine; and
a brace portion coupled to the flexible support proximate ends of the flexible support, the brace portion adapted to force the spring portion toward the spine as a wearer bends; and
a pair of segmented pads coupled to the flexible support, wherein the segmented pads are conformable to a selected body part.

14. The back support system of claim 13 wherein the segmented pads are positioned to conform to shoulders of the wearer.

15. The back support system of claim 13 wherein the segmented pads are positioned to conform to hips of the wearer.

16. A back support system comprising:
a flexible support formed in the shape of a portion of a spine of a person, the flexible support extending in an "S" shape corresponding to the shape of the spine; and
a brace portion coupled to the flexible support proximate ends of the flexible support, the brace portion adapted to force the spring portion toward the spine as a wearer bends; and
a pair of shoulder hooks attached to the brace portion at a top of the brace portion and positioned to engage shoulders of the wearer.

17. The back support system of claim 16 wherein the shoulder hooks are formed of a rigid material.

18. The back support system of claim 16 wherein the shoulder hooks include padding to engage the shoulder of the wearer.

More Examples

1. A back support device comprising:
a flexible support adapted to be positioned adjacent a spine of a wearer, the flexible support extending along the spine in an "S" shape; and
a brace portion coupled to the flexible support at ends of the flexible support, adapted to force the flexible support portion toward the spine as a wearer bends.

2. The back support device of example 1 and further comprising an adjustable tension wire positioned to extend around a wearer and tighten the brace portion against the flexible support portion.

3. The back support device of any of examples 1-2 wherein the adjustable tension wire further includes a tension adjusting control coupled to the wire to releasable tighten the tension wire.

4. The back support device of any of examples 1-3 wherein the adjustable tension wire is coupled to a laminated shield to reside between the wire and a body of a wearer to spread force from the wire over a portion of the body wider than the width of the wire.

5. The back support device of any of examples 1-4 wherein the brace portion contains an opening, and wherein the adjustable tension wire forms a serpentine path about the garment portion.

6. The back support device of any of examples 1-5 wherein the adjustable tension wire is coupled to the brace portion about a portion of the brace portion proximate a lower back portion of a wearer.

7. The back support device of any of examples 1-6 and further comprising an upper adjustable tension wire coupled to the brace portion about an upper portion of the brace portion.

8. The back support device of any of examples 1-7 and further comprising a garment portion disposed between the flexible support portion and the brace portion.

9. The back support device of any of examples 1-8 and further comprising a clamp positioned about a lower end of the brace portion, the clamp adapted to support the back support proximate a wearer's spine by supporting the back support by clothing worn about the waist of the wearer.

10. The back support device of any of examples 1-9 and further comprising a garment having the brace portion and flexible support portion integrated into the garment, and having an upper and a lower lacing integrated into the garment.

11. The back support device of example 10 and further comprising a pair of respective tightening controls coupled to respective upper and lower lacing and supported by the garment in a position accessible to the wearer to control force on the wearer's spine generated by the brace portion pushing the flexible support portion toward the spine.

12. A method comprising:
placing a flexible support adjacent a spine of a wearer, the flexible support extending along the spine in an "S" shape; and
coupling a brace portion to the flexible support at ends of the flexible support, wherein the brace portion is positioned to force the flexible support portion toward the spine as a wearer bends.

13. The method of example 12 and further comprising using an adjustable tension wire positioned to extend around a wearer to tighten the brace portion against the flexible support portion.

14. The method of example 13 wherein tightening is performed using a tension adjusting control coupled to the wire to releasable tighten the tension wire.

15. The method of example 14 wherein the adjustable tension wire is coupled to a laminated shield to reside between the wire and a body of a wearer to spread force from the wire over a portion of the body wider than the width of the wire.

16. The method of example 13 wherein the adjustable tension wire is coupled to the brace portion about a portion of the brace portion proximate a lower back portion of a wearer.

17. The method of example 13 wherein tightening further utilizes an upper adjustable tension wire coupled to the brace portion about an upper portion of the brace portion.

18. The method of any of examples 12-17 and further comprising integrating the flexible support portion and the brace portion into a garment.

19. The method of any of examples 12-18 and further comprising providing a clamp positioned about a lower end of the brace portion, the clamp adapted to support the back support proximate a wearer's spine by supporting the back support by clothing worn about the waist of the wearer.

20. The method of example 12 and further comprising integrating the brace portion and flexible support portion into the garment, and integrating an upper and a lower lacing into the garment with a pair of respective tightening controls coupled to respective upper and lower lacing and supported by the garment in a position accessible to the wearer to control force on the wearer's spine generated by the brace portion pushing the flexible support portion toward the spine.

21. A method for controlling the rigidness and flexibility of an artificial spine device that can assist the user in all-day use. This would have the ability of the back support device to be both flexible and rigid and adjust to the normal body movements of the human spine in moments of walking, siting, and lifting.

22. A method for controlling the rigidness and flexibility of an artificial spine that can assist the user in all-day use. The artificial spine would be placed vertically along the center of the human spine. The flexible support would be bent and shaped to the natural "S" shape of the human lumbar spine. This method would allow the artificial spine to always be pressed against the human spine adding support. Since the material of the flexible support is flexible, it would follow the movement and shape of the lumbar spine.

23. A method of bringing together a garment of overlapping sliding soft material plates using a lacing system to create support for the lower back muscles. The material plates can come together and separate by adjusting the lacing system.

24. A method of attaching the lower part of the flexible support to the top section of the brace portion. This method would create a "hinge" at the fulcrum point of the waist that could control the movement of the user when bending forward to prevent hyperextension. This method would also add needed support and pressure to the lower back muscles as the flexible support follows the "bow" shape of the lumbar spine when bending forward.

25. A method of creating a lacing system that weaves together a garment of soft material plates coupled to the brace portion, and wraps around the torso to connect to the front control dials. This method would allow for a secure adjustable fit of the brace portion and flexible support to be pressed against the human back.

26. The method according to any of examples 21-25 would allow for the back support device (back brace plus artificial spine (spring)) to be inserted or removed from apparel and other types of garments and soft goods.

27. A back support system comprising:
a flexible support formed in the shape of a portion of a spine of a person, the flexible support extending in an "S" shape corresponding to the shape of the spine; and
a brace portion coupled to the flexible support proximate ends of the flexible support, the brace portion adapted to force the spring portion toward the spine as a wearer bends; and
at least one rib extending between the flexible support and the brace portion.

28. The back support system of example 27 wherein the at least one rib extends substantially orthogonally from the brace portion toward the flexible support portion near a middle of a length of the brace portion.

29. The back support system of example 28 wherein the at least one rib extends laterally for substantially an entire width of the brace portion.

30. The back support system of example 29 wherein the at least one rib extends laterally for substantially an entire width of the flexible support.

31. The back support system of any of examples 27-30 wherein the at least one rib comprises multiple ribs, including a center rib that extends substantially orthogonally from the brace portion toward the flexible support portion, a second rib above the center rib that extends at a downward angle from the brace portion toward the flexible support portion, and a third rib below the center rib that extends at an upward angle from the brace portion toward the flexible support portion.

32. The back support system of example 31 wherein the at least one rib comprises further multiple ribs above the second rib and below the third rib, each rib extending at a larger angle the further such ribs are positioned from the center rib.

33. The back support system of any of examples 27-32 wherein the back support system is configured to follow the movement of a wearer as the wearer bends forward such that the flexible support bends forward.

34. The back support system of example 33 wherein responsive to tension being reduced from the flexible support by the wearer's movement, the at least one rib flexes and returns to its original position, pushing the flexible support to also return to its unstressed position.

35. The back support system of any of examples 27-34 and further comprising an adjustable tension wire positioned to extend around a wearer and when tightened, to draw the brace portion towards flexible support, and wherein the adjustable tension wire further includes a tension adjusting control coupled to the wire to releasable tighten the tension wire.

36. The back support system of any of examples 27-35 and further comprising a garment having the brace portion and flexible support portion integrated into the garment, and having an upper and a lower lacing integrated into the garment.

37. The back support system of example 36 and further comprising a pair of respective tightening controls coupled to respective upper and lower lacing and supported by the garment in a position accessible to the wearer to control force on the wearer's spine generated by the brace portion pushing the flexible support portion toward the spine.

38. A method comprising:
placing a flexible support adjacent a spine of a wearer, the flexible support extending in an "S" shape corresponding to the shape of the spine;
coupling a brace portion to the flexible support proximate ends of the flexible support, the brace portion adapted to force the spring portion toward the spine as a wearer bends; and
inhibiting lateral movement of the flexible support and brace portion by providing at least one rib extending between the flexible support and the brace portion.

39. The method of example 38 wherein the at least one rib extends substantially orthogonally from the brace portion toward the flexible support portion near a middle of a length of the brace portion and extends laterally for substantially an entire width of the brace portion.

40. The method of any of examples 38-39 wherein the at least one rib comprises multiple ribs, including a center rib that extends substantially orthogonally from the brace portion toward the flexible support portion, a second rib above the center rib that extends at a downward angle from the brace portion toward the flexible support portion, and a third rib below the center rib that extends at an upward angle from the brace portion toward the flexible support portion, and wherein the multiple ribs cooperate to inhibit lateral movement of the respective flexible support and brace portion along their entire lengths.

41. The method of example 40 wherein the at least one rib comprises further multiple ribs above the second rib and below the third rib, each rib extending at a larger angle the further such ribs are positioned from the center rib, the multiple ribs bend responsive to pressure or tension applied to the flexible support and brace portion.

42. The method of any of examples 38-41 wherein the flexible support follows the movement of a wearer as the wearer bends forward such that the flexible support bends forward.

43. The method of example 42 wherein responsive to pressure or tension on the flexible support and brace portion being reduced from the flexible support by the wearer's movement, the at least one rib flexes and returns to its original position, pushing the flexible support and brace portion to return to an unstressed position.

44. The method of any of examples 38-43 and further comprising adjusting an adjustable tension wire positioned to extend around a wearer to draw the brace portion towards flexible support, and wherein the adjustable tension wire further comprising adjusting a tension adjusting control coupled to the wire to releasable tighten the tension wire.

45. The method of any of examples 38-44 and further comprising integrating the flexible support, brace portion, and one or more ribs into a garment.

46. The method of example 45 and further comprising adjusting a pair of tightening controls coupled to respective upper and lower lacing and supported by the garment in a position accessible to the wearer to control force on the wearer's spine generated by the brace portion pushing the flexible support portion toward the spine.

47. A back support device comprising:
an "S" shaped flexible spring support adapted to be positioned adjacent a spine of a wearer, the flexible spring support extending along the spine of the wearer when worn;
a brace plate including two ends directly coupled to the flexible spring support at ends of the flexible spring support, wherein the brace plate defines a portion that extends directly between one coupled end to the other coupled end, and wherein the portion is positioned behind and spaced from the flexible spring support; and at least one rib extending between the spring support and the brace plate.

48. The back support device of claim 47 wherein the spring support, brace plate, and at least one rib are formed of a single piece of injection molded material.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:
1. A back support system comprising:
a flexible support formed in a shape configured to correspond to a shape of a portion of a spine of a wearer;
a lower brace portion coupled to flexible support proximate ends of the flexible support, the lower brace portion adapted to force the flexible support toward the spine as the wearer bends;
an upper brace portion adjustably coupled to the lower brace portion for adjusting an overall length of the upper and lower brace portions combined; and
multiple ribs, including a center rib that extends substantially orthogonally from the lower brace portion toward the flexible support, a second rib above the center rib that extends at a downward angle from the lower brace portion toward the flexible support, and a third rib below the center rib that extends at an upward angle from the lower brace portion toward the flexible support.

2. The back support system of claim 1 wherein the center rib extends laterally for an entire width of the lower brace portion.

3. The back support system of claim 2 wherein the center rib extends laterally for an entire width of the flexible support.

4. The back support system of claim 1 wherein the back support system is configured to follow a movement of the wearer as the wearer bends forward such that the flexible support bends forward.

5. The back support system of claim 4 wherein responsive to tension being reduced from the flexible support by the wearer's movement, at least one of the multiple ribs flexes and returns to its original position, pushing the flexible support to also return to its unstressed position.

6. The back support system of claim 1 and further comprising a garment having the lower brace portion and flexible support integrated into the garment, and having an upper and a lower lacing integrated into the garment.

7. The back support system of claim 6 and further comprising a pair of respective tightening controls coupled to respective upper and lower lacing and supported by the garment in a position configured to be accessible to the wearer to control a force on the wearer's spine generated by the lower brace portion pushing the flexible support toward the spine.

8. The back support system of claim 1 wherein the center rib extends substantially orthogonally from the lower brace portion toward the flexible support near a middle of a length of the lower brace portion.

9. The back support system of claim 1 wherein the multiple ribs comprise further multiple ribs above the second rib and below the third rib, each rib extending at a larger angle the further such ribs are positioned from the center rib.

10. The back support system of claim 1 and further comprising an adjustable tension wire positioned to extend around the wearer and when tightened, to draw the lower brace portion towards the flexible support, and wherein the adjustable tension wire further includes a tension adjusting control coupled to the adjustable tension wire to releasably tighten the adjustable tension wire.

11. A back support system comprising:
a flexible support formed in the shape of a portion of a spine of a wearer, the flexible support extending in an "S" shape configured to correspond to a shape of the portion of the spine;
a brace portion coupled to flexible support proximate ends of the flexible support, the brace portion adapted to force the flexible support toward the spine as the wearer bends;
a pair of segmented pads coupled to the flexible support, wherein the segmented pads are conformable to a selected body part other than a back of the wearer; and
multiple ribs, including a center rib that extends substantially orthogonally from the brace portion toward the flexible support, a second rib above the center rib that extends at a downward angle from the brace portion toward the flexible support, and a third rib below the center rib that extends at an upward angle from the brace portion toward the flexible support.

12. The back support system of claim 11 wherein the segmented pads are positioned to conform to shoulders of the wearer.

13. The back support system of claim 11 wherein the segmented pads are positioned to conform to hips of the wearer.

14. A back support system comprising:
a flexible support formed in a shape configured to correspond to a shape of a portion of a spine of a wearer;
a brace portion coupled to flexible support proximate ends of the flexible support, the brace portion adapted to force the flexible support toward the spine as the wearer bends; and
multiple ribs, including a center rib that extends substantially orthogonally from the brace portion toward the flexible support, a second rib above the center rib that extends at a downward angle from the brace portion toward the flexible support, and a third rib below the center rib that extends at an upward angle from the brace portion toward the flexible, wherein the back support system is configured to follow a movement of the wearer as the wearer bends forward such that the flexible support applies pressure forward and wherein responsive to tension being reduced from the flexible support by the wearer's movement, at least one of the multiple ribs flexes and returns to its original position, reducing the forward pressure of the flexible support.

* * * * *

UNITED STATES PATENT AND TRADEMARK OFFICE
CERTIFICATE OF CORRECTION

| | | |
|---|---|---|
| PATENT NO. | : 12,364,618 B2 | Page 1 of 1 |
| APPLICATION NO. | : 17/438738 | |
| DATED | : July 22, 2025 | |
| INVENTOR(S) | : Leonardo Ochoa | |

It is certified that error appears in the above-identified patent and that said Letters Patent is hereby corrected as shown below:

On the Title Page

Item (72), in "Inventor", in Column 1, Line 1, delete "Beaverton, WA (US)" and insert --Beaverton, OR (US)-- therefor Signed and Sealed this
Twenty-sixth Day of August, 2025

Coke Morgan Stewart
*Acting Director of the United States Patent and Trademark Office*